(12) United States Patent
Andersen et al.

(10) Patent No.: US 12,071,643 B2
(45) Date of Patent: *Aug. 27, 2024

(54) ALPHA-AMYLASE VARIANTS

(71) Applicant: NOVOZYMES A/S, Bagsvaerd (DK)

(72) Inventors: Carsten Andersen, Vaerloese (DK); Iben Damager, Vaerloese (DK); Chakshusmathi Ghadiyaram, Bangalore (IN); Rajendra Kulothungan Sainathan, Bangalore (IN); Padma Venkatachalam Iyer, Mumbai (IN)

(73) Assignee: NOVOZYMES A/S, Bagsvaerd (DK)

( * ) Notice: Subject to any disclaimer, the term of this patent is extended or adjusted under 35 U.S.C. 154(b) by 136 days.

This patent is subject to a terminal disclaimer.

(21) Appl. No.: 16/482,741

(22) PCT Filed: Jan. 30, 2018

(86) PCT No.: PCT/EP2018/052197
§ 371 (c)(1),
(2) Date: Aug. 1, 2019

(87) PCT Pub. No.: WO2018/141707
PCT Pub. Date: Aug. 9, 2018

(65) Prior Publication Data
US 2019/0345470 A1    Nov. 14, 2019

(30) Foreign Application Priority Data

Feb. 1, 2017  (IN) .............................. 201741003686
Mar. 27, 2017  (EP) ..................................... 17163114

(51) Int. Cl.
| | | |
|---|---|---|
| *C12N 9/24* | (2006.01) | |
| *C12N 9/28* | (2006.01) | |
| *C12N 15/63* | (2006.01) | |

(52) U.S. Cl.
CPC ........... *C12N 9/2417* (2013.01); *C12N 15/63* (2013.01); *C12Y 302/01001* (2013.01)

(58) Field of Classification Search
None
See application file for complete search history.

(56) References Cited

U.S. PATENT DOCUMENTS

2015/0353871 A1  12/2015  Oebro
2016/0312200 A1  10/2016  Andersen

FOREIGN PATENT DOCUMENTS

| EP | 2540824 A1 | 1/2013 |
| EP | 2540825 | * 10/2016 |
| EP | 3121270 A2 | 1/2017 |
| JP | 2004508815 A | 3/2004 |
| WO | 96/23873 A1 | 8/1996 |
| WO | 00/60060 A2 | 10/2000 |
| WO | 2001016349 A1 | 3/2001 |
| WO | 2002010355 A2 | 2/2002 |
| WO | 2013/001078 A1 | 1/2013 |
| WO | WO 2016/180748 | * 11/2016 |

OTHER PUBLICATIONS

Tsukamoto et al, 1988, Biochem Biophys Res Com 151(1), 25-31.

* cited by examiner

*Primary Examiner* — Suzanne M Noakes
(74) *Attorney, Agent, or Firm* — Yoshimi D. Barron

(57) ABSTRACT

The present invention relates to variants of a parent alpha-amylase having an improved wash performance when compared to the parent alpha-amylase. The present invention also relates to polynucleotides encoding the variants, nucleic acid constructs, vectors, and host cells comprising the polynucleotides, and method of producing the variants of the present invention.

17 Claims, No Drawings
Specification includes a Sequence Listing.

ID NO: 1, 2, 3, 4, 5, 6, 7, or 8.

ALPHA-AMYLASE VARIANTS

CROSS-REFERENCE TO RELATED APPLICATIONS

This application is a 35 U.S.C. 371 national application of international application no. PCT/EP2018/052197 filed Jan. 30, 2018, which claims priority or the benefit under 35 U.S.C. 119 of European application no. 17163114.6 filed Mar. 27, 2017 and Indian provisional application no. 201741003686 filed Feb. 1, 2017, the contents of which are fully incorporated herein by reference.

REFERENCE TO A JOINT RESEARCH AGREEMENT

The embodiments claimed in the present application were made under a joint research agreement between The Procter & Gamble Company and Novozymes A/S.

REFERENCE TO A SEQUENCE LISTING

This application contains a Sequence Listing in computer readable form, which is incorporated herein by reference.

BACKGROUND OF THE INVENTION

Field of the Invention

The present invention relates to variants of an alpha-amylase, polynucleotides encoding the variants, and methods of producing the variants.

Description of the Related Art

Alpha-amylases (alpha-1,4-glucan-4-glucanohydrolases, E.C. 3.2.1.1) constitute a group of enzymes, which catalyses hydrolysis of starch and other linear and branched 1,4-gluosidic oligo- and polysaccharides.

There is a long history of industrial use of alpha-amylases in several known applications such as detergent, baking, brewing, starch liquefaction and saccharification e.g. in preparation of high fructose syrups or as part of ethanol production from starch. These and other applications of alpha-amylases are known and utilize alpha-amylases derived from microorganisms, in particular bacterial alpha-amylases.

Among the first bacterial alpha-amylases to be used were an alpha-amylase from *B. licheniformis*, also known as Termamyl which have been extensively characterized and the crystal structure has been determined for this enzyme. Alkaline amylases, such as AA560, form a particular group of alpha-amylases that have found use in detergents. Many of these known bacterial amylases have been modified in order to improve their functionality in a particular application.

*Bacillus* amylases, such as Termamyl, AA560 (WO 2000/060060) and SP707 (described by Tsukamoto et al., 1988, *Biochem. Biophys. Res. Comm.* 151: 25-31) form a particular group of alpha-amylases that have found use in detergents. These amylases have been modified to improve the stability in detergents. WO 96/23873 e.g. disclose to delete the amino acids 181+182 or the amino acids 183+184 of SP707 (SEQ ID NO: 7 of WO 96/23873) to improve the stability of this amylase. WO 96/23873 further discloses to modify the SP707 amylase by substituting M202 with e.g. a leucine to stabilize the molecule towards oxidation. Thus, it is known to modify amylases to improve certain properties.

For environmental reasons it has been increasingly important to lower the temperature in washing, dishwashing and/or cleaning processes. However, most enzymes including amylases have a temperature optimum which is above the temperature usually used in low temperature washing. Alpha-amylase is a key enzyme for use in detergent compositions and its use has become increasingly important for removal of starchy stains during laundry washing or dishwashing. Therefore, it is important to find alpha-amylase variants, which retain their wash performance, stain removal effect and/or activity when the temperature is lowered. However, despite the efficiency of current detergents enzyme compositions, there are many stains that are difficult to completely remove. These problems are compounded by the increased use of low (e.g., cold water) wash temperatures and shorter washing cycles. Thus, it is desirable to have amylolytic enzymes that can function under low temperature and at the same time preserve or increase other desirable properties such as specific activity (amylolytic activity), stability and/or wash performance.

Thus, it is an object of the present invention to provide alpha-amylase variants which could be used in washing, dishwashing and/or cleaning processes at low temperature, such as temperatures of 5-40° C. It is a further object of the present invention to provide alpha-amylase variants which have improved wash performance at low temperature compared to the parent alpha-amylase or compared to the alpha-amylase of any of SEQ ID NO: 1, 2, 3, 4, 5, 6, 7, or 8.

SUMMARY OF THE INVENTION

The present invention relates to a variant of a parent alpha-amylase, wherein the variant comprises (i) a modification at one or more positions corresponding to 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, (ii) the variant has at least 80, such as at least 90%, such as at least 95%, such as at least 97%, but less than 100% sequence identity with the amino acid sequence set forth in SEQ ID NOs: 1, 2, 3, 4, 5, 6, 7, or 8, and (iii) the variant has alpha-amylase activity.

The present invention also relates to a polynucleotide encoding a variant according to the invention, a nucleic acid construct comprising the polynucleotide encoding the variant according to the invention, an expression vector comprising the polynucleotide encoding the variant according to the invention, and a host cell comprising the polynucleotide encoding the variant according to the invention.

The present invention also relates to a method of producing an alpha-amylase variant, comprising (a) cultivating the host cell of the invention under conditions suitable for expression of the variant, and (b) recovering the variant.

The present invention further relates to a method of obtaining an alpha-amylase variant, comprising introducing into a parent alpha-amylase a modification at one or more positions corresponding to 109, 7, 1, 391, 280, 284, 320, and 323 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, wherein each modification is independently a substitution or deletion, and the variant has alpha-amylase activity; and recovering the variant.

DETAILED DESCRIPTION OF THE INVENTION

The present invention relates to variants of a parent alpha-amylase, wherein the variant comprises (i) a modification at one or more positions corresponding to 109, 7, 1, 391, 280, 284, 320, and 323 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO. 1, (ii) the variant has at least 80, such as at least 90%, such as at least 95%, such as at least 97%, but less than 100% sequence identity with the amino acid sequence set forth in SEQ ID NOs: 1, 2, 3, 4, 5, 6, 7, or 8, and (iii) the variant has alpha-amylase activity.

In one aspect, the present invention relates to a variant of a parent alpha-amylase, wherein the variant comprises (i) a modification at one or more positions corresponding to positions selected from the group consisting of 109, 1, 7, 280, 284, 320, 323, and 391 of the amino acid sequence set forth in SEQ ID NO: 1, and optionally in one or more positions corresponding to positions selected from the group consisting of 140, 181, 182, 183, 184, 195, 206, 243, 260, 304, and 476 of the amino acid sequence as set forth in SEQ ID NO. 1, (ii) the variant has at least 80, such as at least 90%, such as at least 95%, such as at least 97%, but less than 100% sequence identity with the amino acid sequence set forth in SEQ ID NOs: 1, 2, 3, 4, 5, 6, 7, or 8, and (iii) the variant has alpha-amylase activity.

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "alpha-amylase" (alpha-1,4-glucan-4-glucano-hydrolase, E.C. 3.2.1.1) constitutes a group of enzymes which catalyzes hydrolysis of starch and other linear and branched 1,4-gluosidic oligo- and polysaccharides. For purposes of the present invention, alpha-amylase activity is determined according to the procedure described in Example section. In one aspect, the variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1.

The term 'amino acid' as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids. Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

When an amino acid is being specifically enumerated, such as 'alanine' or 'Ala' or 'A', the term refers to both l-alanine and d-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid. In one embodiment, the polypeptides of the invention comprise or consist of L-amino acids.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The terms "enhanced wash performance" or "improved wash performance" mean the ability of the polypeptide of the invention to provide a cleaning effect (e.g. stain removal) in a wash process, such as laundry or dishwashing, is improved compared to that of the parent alpha-amylase of SEQ ID NO:1. Wash performance may be determined using methods well known in the art, such as using an automatic mechanical stress assay (AMSA). It will be appreciated by persons skilled in the art that the enhanced wash performance may be achieved under only some or perhaps all wash conditions, for example at wash temperatures of 20° C. or higher (such as at 40° C.).

The term "enzyme detergency benefit" used herein, refers to the advantageous effect an enzyme may add to a detergent compared to the same detergent without the enzyme. Important detergency benefits which can be provided by enzymes are stain removal with no or very little visible soils after washing and/or cleaning, prevention or reduction of re-deposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of re-deposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

The term "expression" includes any step involved in the production of a variant including, but not limited to, transcription, post-transcriptional modification, translation, post-translational modification, and secretion.

The term "expression vector" means a linear or circular DNA molecule that comprises a polynucleotide encoding a variant and is operably linked to control sequences that provide for its expression.

The term "fragment" means a polypeptide having one or more (e.g., several) amino acids absent from the amino and/or carboxyl terminus of the polypeptide of SEQ ID NOs:1, 2, 3, 4, 5, 6, 7, or 8; wherein the fragment has alpha-amylase activity. In one aspect, a fragment contains at least 200 contiguous amino acid residues of SEQ ID NOs: 1, 2, 3, 4, 5, 6, 7, or 8, for example at least 300 contiguous amino acid residues, or at least 350 contiguous amino acid residues, or at least 400 contiguous amino acid residues, or at least 450 contiguous amino acid residues of SEQ ID NO: 1, 2, 3, 4, 5, 6, 7, or 8.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "Intensity value" as used herein, refers to the wash performance measurement. It is measured as the brightness expressed as the intensity of the light reflected from the sample when illuminated with white light. When the sample is stained the intensity of the reflected light is lower, than that of a clean sample. Therefore, the intensity of the reflected light can be used to measure wash performance, where a higher intensity value correlates with higher wash performance. Color measurements are made with a professional flatbed scanner (Kodak iQsmart, Kodak) used to capture an image of the washed textile. To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$\mathrm{Int} = \sqrt{r^2 + g^2 + b^2}$$

The terms "Delta intensity" or "Delta intensity value" are defined herein as the result of an intensity measurement of a test material, e.g. a swatch CS-28 (Center For Testmaterials BV, P.O. Box 120, 3133 KT Vlaardingen, the Netherlands) or a hard surface. The swatch is measured with a portion of the swatch, washed under identical conditions, as background. The delta intensity is the intensity value of the test material washed with amylase subtracting the intensity value of the test material washed without amylase.

The term "improved property" as used herein, refers to a characteristic associated with a variant that is improved compared to the parent. Such improved properties include, but are not limited to, wash performance, thermal activity, thermostability, and stability under storage conditions and chemical stability. The improved property may be any of those herein defined and described, such as stability.

The term "improved wash performance" is defined herein as displaying an alteration of the wash performance of an amylase of the present invention relative to the wash performance of the amylase of SEQ ID NO: 2 or 1, The alteration may e.g. be seen as increased stain removal. Improved wash performance is determined according to Example 1. The wash performance is improved if the Improvement Factor (IF) is above 1.0, preferably above 1.05 in one or more of the conditions listed in example 1 either in model detergent A at 20° C. where the alpha-amylase variant concentration is 0.2 mg/L, or in model detergent A at 40° C. where the alpha-amylase variant concentration is 0.05 mg/L, or in model detergent J at 20° C. where the alpha-amylase variant concentration is 0.2 mg/L, or in model detergent J at 30° C. where the alpha-amylase variant concentration is 0.05 mg/L or in Detergent K at 20° C. where the alpha-amylase variant concentration is 0.2 mg/L. The wash conditions are described in the Example section.

The term "wash performance" includes cleaning in general e.g. hard surface cleaning as in dish wash, but also wash performance on textiles such as laundry, and also industrial and institutional cleaning. Improved wash performance may be measured by comparing the delta intensities as described in the definition herein.

The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample. In one aspect, the present invention relates to an isolated alpha-amylase variant.

Isolated polynucleotide: The term "isolated polynucleotide" means a polynucleotide that is modified by the hand of man. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Isolated variant: The term "isolated variant" means a variant that is modified by the hand of man. In one aspect, the variant is at least 1% pure, e.g., at least 5% pure, at least 10% pure, at least 20% pure, at least 40% pure, at least 60% pure, at least 80% pure, and at least 90% pure, as determined by SDS-PAGE.

Low temperature: "Low temperature" is a temperature of 5-40° C., preferably 5-35° C., preferably 5-30° C., more preferably 5-25° C., more preferably 5-20° C., most preferably 5-15° C., and in particular 5-10° C. In a preferred embodiment, "Low temperature" is a temperature of 10-35° C., preferably 10-30° C., or 10-25° C., or 10-20° C., or 10-15° C.

The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

The term "mature polypeptide coding sequence" means a polynucleotide that encodes a mature polypeptide having alpha-amylase activity.

The term "mutant" means a polynucleotide encoding a variant.

The term "mutation", in the context of the polypeptides of the invention, means that one or more amino acids within the reference amino acid sequence (i.e. SEQ ID NO:1) are altered by substitution with a different amino acid or by deletion. Additionally, the mutation may correspond to an insertion of one or more extra amino acid(s) within the reference amino acid sequence.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences. The term nucleic acid construct is synonymous with the term "expression cassette" when the nucleic acid construct contains the control sequences required for expression of a coding sequence of the present invention.

The term "operably linked" means a configuration in which a control sequence is placed at an appropriate position relative to the coding sequence of a polynucleotide such that the control sequence directs expression of the coding sequence.

The term "parent" or "parent alpha-amylase" means an alpha-amylase to which an alteration is made to produce the enzyme variants of the present invention. The parent may be a naturally occurring (wild-type) polypeptide or a variant thereof. For example, the parent may be the alpha-amylase of SEQ ID NO:1 (known as SP722). Alternatively, it may also mean the alpha-amylase of SEQ ID NO: 2. The parent alpha-amylase may be any suitable alpha-amylase, such as those listed herein as SEQ ID Nos.: 3, 4, 5, 6, 7, and 8.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used may be gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

Alternatively, the parameters used may be gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Starch removing process: The expression "starch removing process" relates to any kind of process whereby starch is removed (or converted) such as in washing processes where starch is removed from textile e.g. textile cleaning such as laundry. A starch removing process could also be hard surface cleaning such as dish wash or it could be cleaning processes in general such as industrial or institutional cleaning. The expression also comprises other starch removing processes or starch conversion, ethanol production, starch liquefaction, textile desizing, paper and pulp production, beer making and detergents in general.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Substantially pure variant: The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well known recombinant methods or by classical purification methods.

The term "subsequence" means a polynucleotide having one or more (e.g., several) nucleotides absent from the 5' and/or 3' end of a mature polypeptide coding sequence; wherein the subsequence encodes a fragment having alpha-amylase activity.

Textile: Textile sample CS-28 (rice starch on cotton) is obtained from Center For Testmaterials BV, P.O. Box 120, 3133 KT Vlaardingen, the Netherlands.

The term "textile care benefits", as used herein, is defined as not being directly related to catalytic stain removal or prevention of re-deposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, color clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

The term "variant" means a polypeptide having alpha-amylase activity comprising a mutation, i.e., a substitution, insertion, and/or deletion, at one or more (e.g., several) positions relative to the 'parent' alpha-amylase of SEQ ID NO:1 or SEQ ID NOs: 2, 3, 4, 5, 6, 7, or 8. A substitution means replacement of the amino acid occupying a position with a different amino acid; a deletion means removal of the amino acid occupying a position; and an insertion means adding an amino acid adjacent to and immediately following the amino acid occupying a position The variants of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 1 or SEQ ID NO: 2.

The term "wild-type" alpha-amylase means an alpha-amylase expressed by a naturally occurring microorganism, such as a bacterium, yeast, or filamentous fungus found in nature.

Conventions for Designation of Variants

The polypeptides of the invention having alpha-amylase activity correspond to variants of an alpha-amylase derived from *Bacillus*, as shown in SEQ ID NOs: 1, 2, 3, 4, 5, 6, 7, or 8.

```
                                              SEQ ID NO: 1
HHNGTNGTMMQYFEWHLPNDGNHWNRLRDDASNLRNRGITAIWIPPAWKG

TSQNDVGYGAYDLYDLGEFNQKGTVRTKYGTRSQLESAIHALKNNGVQVY

GDVVMNHKGGADATENVLAVEVNPNNRNQEISGDYTIEAWTKFDFPGRGN

TYSDFKWRWYHFDGVDWDQSRQFQNRIYKFRGDGKAWDWEVDSENGNYDY

LMYADVDMDHPEVVNELRRWGEWYTNTLNLDGFRIDAVKHIKYSFTRDWL

THVRNATGKEMFAVAEFWKNDLGALENYLNKTNWNHSVFDVPLHYNLYNA
```

```
                        -continued
SNSGGNYDMAKLLNGTVVQKHPMHAVTFVDNHDSQPGESLESFVQEWFKP

LAYALILTREQGYPSVFYGDYYGIPTHSVPAMKAKIDPILEARQNFAYGT

QHDYFDHHNIIGWTREGNTTHPNSGLATIMSDGPGGEKWMYVGQNKAGQV

WHDITGNKPGTVTINADGWANFSVNGGSVSIWVKR
```

For the purposes of the present invention, the polypeptide disclosed in SEQ ID NO: 1 is used to determine the corresponding amino acid residue in another alpha-amylase polypeptide. However, the skilled person would recognize that the sequence of SEQ ID NO: 2 may also be used to determine the corresponding amino acid residue in another alpha-amylase polypeptide. The amino acid sequence of another alpha-amylase is aligned with the mature polypeptide disclosed in SEQ ID NO: 1, and based on the alignment, the amino acid position number corresponding the any amino acid residue in the mature polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other alpha-amylase has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. E.g. the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the alpha-amylase variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of e.g. threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 181 is designated as "Ser181*" or "S181*". Multiple deletions are separated by addition marks ("+"), e.g., "Ser181*+Thr182*" or "S181*+T182*".

Insertions. For an amino acid insertion, the following nomenclature is used: Original amino acid, position, original amino acid, inserted amino acid. Accordingly, the insertion of lysine after e.g. glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple modifications. Variants comprising multiple modifications are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different modifications. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

Parent Alpha-Amylases

The parent alpha-amylase may be a polypeptide with at least 80% sequence identity with the polypeptide set forth in SEQ ID NO: 1.

In one aspect, the parent alpha-amylase has a sequence identity to the polypeptide of SEQ ID NO: 1 of at least 80%, such as at least 85%, at least 90%, e.g. at least 92%, at least 93%, at least 94%, at least 95%, at least 96%, at least 97%, at least 98%, at least 99, or 100%, which has alpha-amylase activity. In one aspect, the amino acid sequence of the parent alpha-amylase differs by no more than ten amino acids, e.g. by five amino acids, by four amino acids, by three amino acids, by two amino acids, and by one amino acid from the polypeptide of SEQ ID NO: 1.

The parent alpha-amylase preferably comprises or consists of the amino acid sequence of SEQ ID NO: 1. In another embodiment, the parent alpha-amylase is an allelic variant of the polypeptide of SEQ ID NO: 1.

The parent alpha-amylase may also be a polypeptide with at least 80% sequence identity with the polypeptide set forth in SEQ ID NO: 2.

In one aspect, the parent alpha-amylase has a sequence identity to the polypeptide of SEQ ID NO: 2 of at least 80%, such as at least 85%, at least 90%, e.g. at least 92%, at least 93%, at least 94%, at least 95%, at least 96%, at least 97%, at least 98%, at least 99, or 100%, which has alpha-amylase activity. In one aspect, the amino acid sequence of the parent alpha-amylase differs by no more than ten amino acids, e.g. by five amino acids, by four amino acids, by three amino acids, by two amino acids, and by one amino acid from the polypeptide of SEQ ID NO: 2.

The parent alpha-amylase preferably comprises or consists of the amino acid sequence of SEQ ID NO: 2. In another embodiment, the parent alpha-amylase is an allelic variant of the polypeptide of SEQ ID NO: 2.

The parent alpha-amylase may also be a polypeptide with at least 80% sequence identity with the polypeptide set forth in SEQ ID NO: 3.

In one aspect, the parent alpha-amylase has a sequence identity to the polypeptide of SEQ ID NO: 3 of at least 80%, such as at least 85%, at least 90%, e.g. at least 92%, at least 93%, at least 94%, at least 95%, at least 96%, at least 97%, at least 98%, at least 99, or 100%, which has alpha-amylase activity. In one aspect, the amino acid sequence of the parent alpha-amylase differs by no more than ten amino acids, e.g. by five amino acids, by four amino acids, by three amino acids, by two amino acids, and by one amino acid from the polypeptide of SEQ ID NO: 3.

The parent alpha-amylase preferably comprises or consists of the amino acid sequence of SEQ ID NO: 3. In another embodiment, the parent alpha-amylase is an allelic variant of the polypeptide of SEQ ID NO: 3.

The parent alpha-amylase may also be a polypeptide with at least 80% sequence identity with the polypeptide set forth in SEQ ID NO: 4.

In one aspect, the parent alpha-amylase has a sequence identity to the polypeptide of SEQ ID NO: 4 of at least 80%, such as at least 85%, at least 90%, e.g. at least 92%, at least 93%, at least 94%, at least 95%, at least 96%, at least 97%, at least 98%, at least 99, or 100%, which has alpha-amylase activity. In one aspect, the amino acid sequence of the parent alpha-amylase differs by no more than ten amino acids, e.g. by five amino acids, by four amino acids, by three amino acids, by two amino acids, and by one amino acid from the polypeptide of SEQ ID NO: 4.

The parent alpha-amylase preferably comprises or consists of the amino acid sequence of SEQ ID NO: 4. In another embodiment, the parent alpha-amylase is an allelic variant of the polypeptide of SEQ ID NO: 4.

The parent alpha-amylase may also be a polypeptide with at least 80% sequence identity with the polypeptide set forth in SEQ ID NO: 5.

In one aspect, the parent alpha-amylase has a sequence identity to the polypeptide of SEQ ID NO: 5 of at least 80%, such as at least 85%, at least 90%, e.g. at least 92%, at least 93%, at least 94%, at least 95%, at least 96%, at least 97%, at least 98%, at least 99, or 100%, which has alpha-amylase activity. In one aspect, the amino acid sequence of the parent alpha-amylase differs by no more than ten amino acids, e.g. by five amino acids, by four amino acids, by three amino acids, by two amino acids, and by one amino acid from the polypeptide of SEQ ID NO: 5.

The parent alpha-amylase preferably comprises or consists of the amino acid sequence of SEQ ID NO: 5. In another embodiment, the parent alpha-amylase is an allelic variant of the polypeptide of SEQ ID NO: 5.

The parent alpha-amylase may also be a polypeptide with at least 80% sequence identity with the polypeptide set forth in SEQ ID NO: 6.

In one aspect, the parent alpha-amylase has a sequence identity to the polypeptide of SEQ ID NO: 6 of at least 80%, such as at least 85%, at least 90%, e.g. at least 92%, at least 93%, at least 94%, at least 95%, at least 96%, at least 97%, at least 98%, at least 99, or 100%, which has alpha-amylase activity. In one aspect, the amino acid sequence of the parent alpha-amylase differs by no more than ten amino acids, e.g. by five amino acids, by four amino acids, by three amino acids, by two amino acids, and by one amino acid from the polypeptide of SEQ ID NO: 6.

The parent alpha-amylase preferably comprises or consists of the amino acid sequence of SEQ ID NO: 6. In another embodiment, the parent alpha-amylase is an allelic variant of the polypeptide of SEQ ID NO: 6.

The parent alpha-amylase may also be a polypeptide with at least 80% sequence identity with the polypeptide set forth in SEQ ID NO: 7.

In one aspect, the parent alpha-amylase has a sequence identity to the polypeptide of SEQ ID NO: 7 of at least 80%, such as at least 85%, at least 90%, e.g. at least 92%, at least 93%, at least 94%, at least 95%, at least 96%, at least 97%, at least 98%, at least 99, or 100%, which has alpha-amylase activity. In one aspect, the amino acid sequence of the parent alpha-amylase differs by no more than ten amino acids, e.g. by five amino acids, by four amino acids, by three amino acids, by two amino acids, and by one amino acid from the polypeptide of SEQ ID NO: 7.

The parent alpha-amylase preferably comprises or consists of the amino acid sequence of SEQ ID NO: 7. In another embodiment, the parent alpha-amylase is an allelic variant of the polypeptide of SEQ ID NO: 7.

The parent alpha-amylase may also be a polypeptide with at least 80% sequence identity with the polypeptide set forth in SEQ ID NO: 8.

In one aspect, the parent alpha-amylase has a sequence identity to the polypeptide of SEQ ID NO: 8 of at least 80%, such as at least 85%, at least 90%, e.g. at least 92%, at least 93%, at least 94%, at least 95%, at least 96%, at least 97%, at least 98%, at least 99, or 100%, which has alpha-amylase activity. In one aspect, the amino acid sequence of the parent alpha-amylase differs by no more than ten amino acids, e.g. by five amino acids, by four amino acids, by three amino acids, by two amino acids, and by one amino acid from the polypeptide of SEQ ID NO: 8.

The parent alpha-amylase preferably comprises or consists of the amino acid sequence of SEQ ID NO: 8. In another embodiment, the parent alpha-amylase is an allelic variant of the polypeptide of SEQ ID NO: 8.

The amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material, which is used in a Southern blot.

For purposes of the present invention, hybridization indicates that the polynucleotide hybridizes to a labeled nucleotide probe corresponding to a polynucleotide encoding SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or a subsequence thereof, under low to very high stringency conditions. Molecules to which the probe hybridizes can be detected using, for example, X-ray film or any other detection means known in the art.

In one aspect, the nucleic acid probe is a polynucleotide that encodes the polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or a fragment thereof.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The parent may be obtained from microorganisms of any genus. For purposes of the present invention, the term "obtained from" as used herein in connection with a given source shall mean that the parent encoded by a polynucleotide is produced by the source or by a cell in which the polynucleotide from the source has been inserted. In one aspect, the parent is secreted extracellularly.

The parent may be a bacterial alpha-amylase. For example, the parent may be a gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* alpha-amylase, or a gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* alpha-amylase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* alpha-amylase.

In another aspect, the parent is a *Streptococcus equisimilis, Streptococcus pyogenes, Streptococcus uberis*, or *Streptococcus equi* subsp. *Zooepidemicus* alpha-amylase.

In another aspect, the parent is a *Streptomyces achromogenes, Streptomyces avermitilis, Streptomyces coelicolor, Streptomyces griseus*, or *Streptomyces lividans* alpha-amylase.

In another aspect, the parent is a *Bacillus* sp. alpha-amylase, e.g., the alpha-amylase of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. The polynucleotide encoding a parent may then be derived by similarly screening a genomic or cDNA library of another microorganism or mixed DNA sample. Once a polynucleotide encoding a parent has been detected with a probe(s), the polynucleotide may be isolated or cloned by utilizing techniques that are known to those of ordinary skill in the art (see, e.g., Sambrook et al., 1989, supra).

The parent may be a hybrid polypeptide in which a portion of one polypeptide is fused at the N-terminus or the C-terminus of a portion of another polypeptide.

The parent may also be a fused polypeptide or cleavable fusion polypeptide in which one polypeptide is fused at the N-terminus or the C-terminus of another polypeptide. A fused polypeptide is produced by fusing a polynucleotide encoding one polypeptide to a polynucleotide encoding another polypeptide. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J*. 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol*. 3: 568-576; Svetina et al., 2000, *J. Biotechnol*. 76: 245-251; Rasmussen-Wilson et al., 1997, *Appl. Environ. Microbiol*. 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Preparation of Variants

The present invention relates to methods for obtaining a variant having alpha-amylase activity, comprising (a) introducing into a parent alpha-amylase a modification at one or more positions corresponding to positions 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, wherein each modification is independently a substitution or deletion, and said variant has alpha-amylase activity; and (b) recovering said variant.

In one aspect, the invention relates to a method for obtaining a variant having alpha-amylase activity, comprising (a) introducing into a parent alpha-amylase a modification at one or more positions corresponding to positions 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NOs: 2, 3, 4, 5, 6, 7, of 8, wherein the numbering is according to SEQ ID NO: 1, and wherein each modification is independently a substitution or deletion, and said variant has alpha-amylase activity; and (b) recovering said variant.

In one embodiment, the modification is a substitution. In one embodiment, the modification is a deletion.

In another embodiment, the invention relates to a method for obtaining a variant having alpha-amylase activity, comprising (a) introducing into a parent alpha-amylase a substitution at one or more positions, wherein the substitution is selected from H1A, G7A, G109A, N280S, W284H, K320A, M323N, and E391A of the polypeptide of SEQ ID NOs: 1, 2, 3, 4, 5, 6, 7, or 8, wherein numbering is according to SEQ ID NO: 1 and (b) recovering the variant.

In one embodiment, the method further comprises introducing to the parent alpha-amylase a deletion in one or more positions, wherein the deletion is selected from: H1*, R181*, G182*, D183*, and G184* of the polypeptide of SEQ ID Nos: 1, 2, 3, 4, 5, 6, 7, or 8, wherein numbering is according to SEQ ID NO: 1, and recovering the variant.

In one embodiment, the method further comprises introducing to the parent alpha-amylase a substitution in one or more positions, wherein the substitution is selected from: W140Y, N195F, V206Y, Y243F, E260G, G304R, and G476K of the polypeptide of SEQ ID Nos.: 1, 3, 4, 5, 6, 7, or 8, and recovering the variant.

The variants may be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (several) mutations are created at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. See, e.g., Scherer and Davis, 1979, Proc. Natl. Acad. Sci. USA 76: 4949-4955; and Barton et al., 1990, Nucleic Acids Res. 18: 7349-4966.

Site-directed mutagenesis can also be accomplished in vivo by methods known in the art. See, e.g., U.S. Patent Application Publication No. 2004/0171154; Storici et al., 2001, Nature Biotechnol. 19: 773-776; Kren et al., 1998, Nat. Med. 4: 285-290; and Calissano and Macino, 1996, Fungal Genet. Newslett. 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Variants

The present invention also provides variants of a parent alpha-amylase comprising (i) a modification at one or more positions corresponding to positions 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, (ii) the variant has at least 80%, such as at least 90%, such as at least 95%, such as at least 97%, but less than 100% sequence identity with the amino acid sequence set forth in SEQ ID NOs: 1, 2, 3, 4, 5, 6, 7, or 8, and (iii) the variant has alpha-amylase activity. Hereby, variants are provided which has improved washing performance at low temperature, compared to the parent alpha-amylase or compared to the alpha-amylase of SEQ ID NO: 1, 2, 3, 4, 5, 6, 7, or 8.

In an embodiment, the variant has a sequence identity of at least 80%, such as at least 85%, at least 90%, at least 95%, at least 96%, at least 97%, at least 98%, or at least 99%, but less than 100%, to the amino acid sequence of the parent alpha-amylase.

In another embodiment, the invention relates to isolated variants of a parent alpha-amylase comprising (i) a modification at one or more positions corresponding to positions 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, (ii) the variant has at least 80, such as at least 90%, such as at least 95%, such as at least 97%, but less than 100% sequence identity with the amino acid sequence set forth in SEQ ID NOs: 1, 2, 3, 4, 5, 6, 7, or 8, and (iii) the variant has alpha-amylase activity.

In another embodiment, the variant has at least 80%, such as at least 85%, at least 90%, at least 95%, such as at least 96%, at least 97%, at least 98%, and at least 99%, but less than 100%, sequence identity with the mature polypeptide of SEQ ID NO: 1.

In another embodiment, the variant has at least 80%, such as at least 85%, at least 90%, at least 95%, such as at least 96%, at least 97%, at least 98%, and at least 99%, but less than 100%, sequence identity with the mature polypeptide of SEQ ID NO: 2.

In another embodiment, the variant has at least 80%, such as at least 85%, at least 90%, at least 95%, such as at least 96%, at least 97%, at least 98%, and at least 99%, but less than 100%, sequence identity with the mature polypeptide of SEQ ID NO: 3.

In another embodiment, the variant has at least 80%, such as at least 85%, at least 90%, at least 95%, such as at least 96%, at least 97%, at least 98%, and at least 99%, but less than 100%, sequence identity with the mature polypeptide of SEQ ID NO: 4.

In another embodiment, the variant has at least 80%, such as at least 85%, at least 90%, at least 95%, such as at least 96%, at least 97%, at least 98%, and at least 99%, but less than 100%, sequence identity with the mature polypeptide of SEQ ID NO: 5.

In another embodiment, the variant has at least 80%, such as at least 85%, at least 90%, at least 95%, such as at least 96%, at least 97%, at least 98%, and at least 99%, but less than 100%, sequence identity with the mature polypeptide of SEQ ID NO: 6.

In another embodiment, the variant has at least 80%, such as at least 85%, at least 90%, at least 95%, such as at least 96%, at least 97%, at least 98%, and at least 99%, but less than 100%, sequence identity with the mature polypeptide of SEQ ID NO: 7.

In another embodiment, the variant has at least 80%, such as at least 85%, at least 90%, at least 95%, such as at least 96%, at least 97%, at least 98%, and at least 99%, but less than 100%, sequence identity with the mature polypeptide of SEQ ID NO: 8.

In one embodiment, the number of modifications in the variants of the present invention is 1 to 20, e.g., 1 to 10 and 1 to 5, such as 1, 2, 3, 4, 5, 6, 7, 8, 9 or 10 modifications.

In one embodiment, the variant comprises a modification, such as a substitution, at one or more positions corresponding to positions 109, 1, 7, 280, 284, 320, 323, and 391, and optionally a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at two or more positions corresponding to positions 109, 1, 7, 280, 284, 320, 323, and 391, and optionally a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at three or more positions corresponding to positions 109, 1, 7, 280, 284, 320, 323, and 391, and optionally a modification at one or more positions corresponding to positions 140, 181, 182, 183, 184, 195, 203, 243, 260, 304, and 476, wherein numbering is according to SEQ ID NO: 1. In another embodiment, the variant comprises a modification, such as a substitution, at four or more positions corresponding to positions 109, 1, 7, 280, 284, 320, 323, and 391, and optionally a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at five or more positions corresponding to positions 109, 1, 7, 280, 284, 320, 323, and 391, and optionally a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at six or more positions corresponding to positions 109, 1, 7, 280, 284, 320, 323, and 391, and optionally a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at seven or more positions corresponding to positions 109, 1, 7, 280, 284, 320, 323, and 391, and optionally a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at eight positions corresponding to positions 109, 1, 7, 280, 284, 320, 323, and 391, and optionally a modification at one or more positions corresponding to positions 140, 181, 182, 183, 184, 195, 203, 243, 260, 304, and 476, wherein numbering is according to SEQ ID NO: 1.

In one embodiment, the variant comprises a modification, such as a substitution, at one or more positions corresponding to positions 109, 1, 7, 280, 284, 320, 323, and 391, and a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at two or more positions corresponding to positions 109, 1, 7, 280, 284, 320, 323, and 391, and a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at three or more positions corresponding to positions 109, 1, 7, 280, 284, 320, 323, and 391, and a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at four or more positions corresponding to positions 109, 1, 7, 280, 284, 320, 323, and 391, and a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at five or more positions corresponding to positions 109, 1, 7, 280, 284, 320, 323, and 391, and a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at six or more positions corresponding to positions 109, 1, 7, 280, 284, 320, 323, and 391, and a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at seven or more positions corresponding to positions 109, 1, 7, 280, 284, 320, 323, and 391, and a modification at one or more positions corresponding to positions 140, 181, 182, 183, 184, 195, 203, 243, 260, 304, and 476, wherein numbering is according to SEQ ID NO: 1.

In another embodiment, the variant comprises a modification, such as a substitution, at eight positions corresponding to positions 109, 1, 7, 280, 284, 320, 323, and 391, and a modification at one or more positions corresponding to positions 140, 181, 182, 183, 184, 195, 203, 243, 260, 304, and 476, wherein numbering is according to SEQ ID NO: 1.

In a preferred embodiment, the variant comprises a modification in one, two, three, four, or five positions selected from the group consisting of 1, 7, 109, 280, and 391.

In one embodiment, the variant comprises at least one deletion and at least one substitution in two, three, four or five positions selected from the group consisting of 1, 7, 109, 280, and 391.

In one embodiment, the variant comprises a substitution at one, two, three, or four positions selected from 7, 109, 280, and 391.

In one embodiment, the variant comprises modifications in the positions selected from the group of positions consisting of: X1+X7; X1+X109; X1+X280; X1+X284; X1+X320; X1+X323; X1+X391; X109+X280; X109+X284; X109+X320; X109+X323; X109+X391; X7+X109; X7+X280; X7+X284; X7+X320; X7+X323; X7+X391; X280+X284; X280+X320; X280+X323; X280+X391; X284+X320; X284+X323; X284+X391; X320+X323; X320+X391; and X323+X391, wherein numbering is according to SEQ ID NO: 1.

In one embodiment, the variant comprises modifications in the positions selected from the group of positions consisting of: X109+X7+X1; X109+X7+X391; X109+X7+X280; X109+X7+X284; X109+X7+X320; X109+X7+X323; X109+X1+X391; X109+X1+X280; X109+X1+X284; X109+X1+X320; X109+X1+X323; X109+X391+X280; X109+X391+X284; X109+X391+X320; X109+X391+X323; X109+X280+X284; X109+X280+X320; X109+X280+X323; X109+X284+X320; X109+X284+X323; X109+X320+X323; X7+X1+X391; X7+X1+X280; X7+X1+X284; X7+X1+X320; X7+X1+X323; X7+X391+X280; X7+X391+X284; X7+X391+X320; X7+X391+X323; X7+X280+X284; X7+X280+X320; X7+X280+X323; X7+X284+X320; X7+X284+X323; X7+X320+X323; X1+X391+X280; X1+X391+X284; X1+X391+X320; X1+X391+X323; X1+X280+X284; X1+X280+X320; X1+X280+X323; X1+X284+X320; X1+X284+X323; X1+X320+X323; X391+X280+X284; X391+X280+X320; X391+X280+X323; X391+X284+X320; X391+X284+X323; X391+X320+X323; X280+X284+X320; X280+X284+X323; X280+X320-X323; and X284+X320+X323, wherein numbering is according to SEQ ID NO: 1.

In one embodiment, the variant comprises modifications in the positions selected from the group of positions consisting of: X109+X7+X1+X391; X109+X7+X1+X280; X109+X7+X1+X284; X109+X7+X1+X320; X109+X7+X1+X323; X109+X7+X391+X280; X109+X7+X391+X284; X109+X7+X391+X320; X109+X7+X391+X323; X109+X7+X280+X284; X109+X7+X280+X320; X109+X7+X280+X323; X109+X7+X284+X320; X109+X7+X284+X323; X109+X7+X320+X323; X109+X1+X391+X280; X109+X1+X391+X284; X109+X1+X391+X320; X109+X1+X391+X323; X109+X1+X280+X284; X109+X1+X280+X320; X109+X1+X280+X323; X109+X1+X284+X320; X109+X1+X284+X323; X109+X1+X320+X323; X109+X391+X280+X284; X109+X391+X280+X320; X109+X391+X280+X323; X109+X391+X284+X320; X109+X391+X284+X323; X109+X391+X320+X323; X109+X280+X284+X320; X109+X280+X284+X323; X109+X280+X320+X323; X109+X284+X320+X323; X7+X1+X391+X280; X7+X1+X391+X284; X7+X1+X391+X320; X7+X1+X391+X323; X7+X1+X280+X284; X7+X1+X280+X320; X7+X1+X280+X323; X7+X1+X284+X320; X7+X1+X284+X323; X7+X1+X320+X323; X7+X391+X280+X284; X7+X391+X280+X320; X7+X391+X280+X323; X7+X391+X284+X320; X7+X391+X284+X323; X7+X391+X320+X323; X7+X280+X284+X320; X7+X280+X284+X323; X7+X280+X320+X323; X7+X284+X320+X323; X1+X391+X280+X284; X1+X391+X280+X320; X1+X391+X280+X323; X1+X391+X284+X320; X1+X391+X284+X323; X1+X391+X320+X323; X1+X280+X284+X320; X1+X280+X284+X323; X1+X280+X320+X323; X1+X284+X320+X323; X391+X280+X284+X320; X391+X280+X284+X323; X391+X280+X320+X323; X391+X284+X320+X323; and X280+X284+X320+X323, wherein numbering is according to SEQ ID NO: 1.

In one embodiment, the variant comprises one or more modifications selected from the group consisting of X1*, X1A, X7A, X7K, X7E, X7N. X7Q, X7L, X7D, X109A, X109S, X140Y, X181*, X182*, X183*, X184*, X195F, X206Y, X243F, X260G, X280S, X284H, X284R, X284F, X304R, X320A, X320M, X320T, X320V, X320S, X323N, X323R, X323S, X323K, X391A, X391V, and X476K, wherein numbering is according to SEQ ID NO: 1.

In one particular embodiment, the variant comprises the modifications selected from the group consisting of: X1*+X1A; X1*+X7A; X1*+X109A; X1*+X280S; X1*+X284H; X1*+X320A; X1*+X323N; X1*+X391A; X1A+X7A; X1A+X109A; X1A+X280S; X1A+X284H; X1A+X320A; X1A+X323N; X1A+X391A; X7A+X109A; X7A+X280S; X7A+X284H; X7A+X320A; X7A+X323N; X7A+X391A; X109A+X280S; X109A+X284H; X109A+X320A; X109A+X323N; X109A+X391A; X280S+X284H; X280S+X320A; X280S+X323N; X280S+X391A; X284H+X320A; X284H+X323N; X284H+X391A; X320A+X323N; X320A+X391A; and X323N+X391A, wherein numbering is according to SEQ ID NO: 1.

In one embodiment, the variant comprises the modifications selected from the group consisting of: X1*+X7A+X109A; X1*+X7A+X280S; X1*+X7A+X284H; X1*+X7A+X320A; X1*+X7A+X323N; X1*+X7A+X391A; X1*+X109A+X280S; X1*+X109A+X284H; X1*+X109A+X320A; X1*+X109A+X323N; X1*+X109A+X391A; X1*+X280S+X284H; X1*+X280S+X320A; X1*+X280S+X323N; X1*+X280S+X391A; X1*+X284H+X320A; X1*+X284H+X323N; X1*+X284H+X391A; X1*+X320A+X323N; X1*+X320A+X391A; X1*+X323N+X391A; X1A+X7A+X109A; X1A+X7A+X280S; X1A+X7A+X284H; X1A+X7A+X320A; X1A+X7A+X323N; X1A+X7A+X391A; X1A+X109A+X280S; X1A+X109A+X284H; X1A+X109A+X320A; X1A+X109A+X323N; X1A+X109A+X391A; X1A+X280S+X284H; X1A+X280S+X320A; X1A+X280S+X323N; X1A+X280S+X391A; X1A+X284H+X320A; X1A+X284H+X323N; X1A+X284H+X391A; X1A+X320A+X323N; X1A+X320A+X391A; X1A+X323N+X391A; X7A+X109A+X280S; X7A+X109A+X284H; X7A+X109A+X320A; X7A+X109A+X323N; X7A+X109A+X391A; X7A+X280S+X284H; X7A+X280S+X320A; X7A+X280S+X323N; X7A+X280S+X391A; X7A+X284H+X320A; X7A+X284H+X323N; X7A+X284H+X391A; X7A+X320A+X323N; X7A+X320A+X391A; X7A+X323N+X391A; X109A+X280S+X284H; X109A+X280S+X320A; X109A+X280S+X323N; X109A+X280S+X391A; X109A+X284H+X320A; X109A+X284H+X323N; X109A+X284H+X391A; X109A+X320A+X323N; X109A+

X320A+X391A; X109A+X323N+X391A; X280S+ X284H+X320A; X280S+X284H+X323N; X280S+X284H+ X391A; X280S+X320A+X323N; X280S+X320A+X391A; X280S+X323N+X391A; X284H+X320A+X323N; X284H+X320A+X391A; X284H+X323N+X391A; and X320A+X323N+X391A, wherein numbering is according to SEQ ID NO: 1.

In one preferred embodiment, the variant comprises modifications in the positions corresponding to the positions selected from the group consisting of:

X1*+X109A+X280S+X391A; X1*+X7K+X109A+ X280S+X391A; X1*+X7E+X109A+X280S+X391A; X1*+X7N+X109A+X280S+X391A; X1*+X7Q+ X109A+X280S+X391A; X1*+X7L+X109A+X280S+ X391A; X1*+X7D+X109A+X280S+X391A; X1*+ X109A+X280S+X320A+X391A; X1*+X109A+ X280S+X320M+X391A; X1*+X109A+X280S+ X320T+X391A; X1*+X109A+X280S+X320V+ X391A; X1*+X109A+X280S+X323R+X391A; X1*+ X109A+X280S+X320S+X391A; X1*+X109A+ X280S+X391V; X1*+X109A+X284R+X391A; X1*+ X109A+X284F+X391A; X1*+X109A+X280S+ X320A+X323S+X391A; X1*+X109A+X280S+ X284F+X391A; X1*+X109A+X280S+X323N+ X391A; X1*+X109A+X280S+X323K+X391A; X1*+ X109S+X280S+X391A; X1*+X109A+X284H+ X391A; X1*+X109A+X280S+X320A+X323N+ X391A; X1*+X7A+X109A+X280S+X391A; X1*+ X7A+X109A+X280S+X284H+X320A+X323N+ X391A; X7A+X284H+X320A+X323N; X7A+ X320A+X323N; X320A; X7A+X320A; X1*+X7A+ X109A+X280S+X391A; X1*+X109A+X280S+ X284H+X391A; X1*+X109A+X280S+X323S+ X391A; X1*+X7A+X109A+X280S+X320A+X391A; X1*+X7A+X109A+X280S+X323S+X391A; X1*+ X7A+X109A+X280S+X323N+X391A; X1*+X7A+ X109A+X280S+X284F+X391A; X1*+X7A+X109A+ X280S+X284R+X391A; X1*+X7A+X109A+X280S+ X320A+X323S+X391A; X1*+X7A+X109A+X284R+ X391A; and X1*+X7A+X109A+X280S+X320A+ X323N+X391A, wherein numbering is according to SEQ ID NO: 1 and the variant has at least 80% sequence identity to any one of the amylases set forth in SEQ ID Nos: 1, 2, 3, 4, 5, 6, 7, or 8.

In one embodiment, the variant comprises modifications in the positions corresponding to the positions of the amino acid sequence set forth in SEQ ID NO: 1, selected from the group consisting of:

X1*+X109A+X280S+X391A; X1*+X7K+X109A+ X280S+X391A; X1*+X7E+X109A+X280S+X391A; X1*+X7N+X109A+X280S+X391A; X1*+X7Q+ X109A+X280S+X391A; X1*+X7L+X109A+X280S+ X391A; X1*+X7D+X109A+X280S+X391A; X1*+ X109A+X280S+X320A+X391A; X1*+X109A+ X280S+X320M+X391A; X1*+X109A+X280S+ X320T+X391A; X1*+X109A+X280S+X320V+ X391A; X1*+X109A+X280S+X323R+X391A; X1*+ X109A+X280S+X320S+X391A; X1*+X109A+ X280S+X391V; X1*+X109A+X284R+X391A; X1*+ X109A+X284F+X391A; X1*+X109A+X280S+ X320A+X323S+X391A; X1*+X109A+X280S+ X284F+X391A; X1*+X109A+X280S+X323N+ X391A; X1*+X109A+X280S+X323K+X391A; X1*+ X109S+X280S+X391A; X1*+X109A+X284H+ X391A; X1*+X109A+X280S+X320A+X323N+ X391A; X1*+X7A+X109A+X280S+X391A; X1*+ X7A+X109A+X280S+X284H+X320A+X323N+ X391A; X7A+X284H+X320A+X323N; X7A+ X320A+X323N; X320A; X7A+X320A; X1*+X7A+ X109A+X280S+X391A; X1*+X109A+X280S+ X284H+X391A; X1*+X109A+X280S+X323S+ X391A; X1*+X7A+X109A+X280S+X320A+X391A; X1*+X7A+X109A+X280S+X323S+X391A; X1*+ X7A+X109A+X280S+X323N+X391A; X1*+X7A+ X109A+X280S+X284F+X391A; X1*+X7A+X109A+ X280S+X284R+X391A; X1*+X7A+X109A+X280S+ X320A+X323S+X391A; X1*+X7A+X109A+X284R+ X391A; and X1*+X7A+X109A+X280S+X320A+ X323N+X391A, wherein numbering is according to SEQ ID NO: 1 and the variant has at least 80% sequence identity to the amylases set forth in SEQ ID NO: 1.

In one embodiment, the variant comprises modifications in the positions corresponding to the positions of the amino acid sequence set forth in SEQ ID NO: 2, wherein the amino acid numbering is according to SEQ ID NO: 1, selected from the group consisting of:

X1*+X109A+X280S+X391A; X1*+X7K+X109A+ X280S+X391A; X1*+X7E+X109A+X280S+X391A; X1*+X7N+X109A+X280S+X391A; X1*+X7Q+ X109A+X280S+X391A; X1*+X7L+X109A+X280S+ X391A; X1*+X7D+X109A+X280S+X391A; X1*+ X109A+X280S+X320A+X391A; X1*+X109A+ X280S+X320M+X391A; X1*+X109A+X280S+ X320T+X391A; X1*+X109A+X280S+X320V+ X391A; X1*+X109A+X280S+X323R+X391A; X1*+ X109A+X280S+X320S+X391A; X1*+X109A+ X280S+X391V; X1*+X109A+X284R+X391A; X1*+ X109A+X284F+X391A; X1*+X109A+X280S+ X320A+X323S+X391A; X1*+X109A+X280S+ X284F+X391A; X1*+X109A+X280S+X323N+ X391A; X1*+X109A+X280S+X323K+X391A; X1*+ X109S+X280S+X391A; X1*+X109A+X284H+ X391A; X1*+X109A+X280S+X320A+X323N+ X391A; X1*+X7A+X109A+X280S+X391A; X1*+ X7A+X109A+X280S+X284H+X320A+X323N+ X391A; X7A+X284H+X320A+X323N; X7A+ X320A+X323N; X320A; X7A+X320A; X1*+X7A+ X109A+X280S+X391A; X1*+X109A+X280S+ X284H+X391A; X1*+X109A+X280S+X323S+ X391A; X1*+X7A+X109A+X280S+X320A+X391A; X1*+X7A+X109A+X280S+X323S+X391A; X1*+ X7A+X109A+X280S+X323N+X391A; X1*+X7A+ X109A+X280S+X284F+X391A; X1*+X7A+X109A+ X280S+X284R+X391A; X1*+X7A+X109A+X280S+ X320A+X323S+X391A; X1*+X7A+X109A+X284R+ X391A; and X1*+X7A+X109A+X280S+X320A+ X323N+X391A, wherein numbering is according to SEQ ID NO: 1 and the variant has at least 80% sequence identity to the amylases set forth in SEQ ID NO: 2.

In one preferred embodiment, the variant comprises modifications in the positions corresponding to the positions of the amino acid sequence set forth in SEQ ID NO: 2, wherein the amino acid numbering is according to SEQ ID NO: 1, selected from the group consisting of:

H1*+G109A+N280S+E391A; H1*+G7K+G109A+ N280S+E391A; H1*+G7E+G109A+N280S+E391A; H1*+G7N+G109A+N280S+E391A; H1*+G7Q+ G109A+N280S+E391A; H1*+G7L+G109A+N280S+ E391A; H1*+G7D+G109A+N280S+E391A; H1*+ G109A+N280S+K320A+E391A; H1*+G109A+ N280S+K320M+E391A; H1*+G109A+N280S+ K320T+E391A; H1*+G109A+N280S+K320V+

E391A; H1*+G109A+N280S+M323R+E391A; H1*+G109A+N280S+K320S+E391A; H1*+G109A+N280S+E391V; H1*+G109A+W284R+E391A; H1*+G109A+W284F+E391A; H1*+G109A+N280S+K320A+M323S+E391A; H1*+G109A+N280S+W284F+E391A; H1*+G109A+N280S+M323N+E391A; H1*+G109A+N280S+M323K+E391A; H1*+G109S+N280S+E391A; H1*+G109A+W284H+E391A; H1*+G109A+N280S+K320A+M323N+E391A; H1*+G7A+G109A+N280S+E391A; H1*+G7A+G109A+N280S+W284H+K320A+M323N+E391A; G7A+W284H+K320A+M323N; G7A+K320A+M323N; K320A; G7A+K320A; H1*+G7A+G109A+N280S+E391A; H1*+G109A+N280S+W284H+E391A; H1*+G109A+N280S+M323S+E391A; H1*+G7A+G109A+N280S+K320A+E391A; H1*+G7A+G109A+N280S+M323S+E391A; H1*+G7A+G109A+N280S+M323N+E391A; H1*+G7A+G109A+N280S+W284F+E391A; H1*+G7A+G109A+N280S+W284R+E391A; H1*+G7A+G109A+N280S+K320A+M323S+E391A; H1*+G7A+G109A+W284R+E391A; and H1*+G7A+G109A+N280S+K320A+M323N+E391A.

In one embodiment, the variant comprises modifications in the positions corresponding to the positions of the amino acid sequence set forth in SEQ ID NO: 3, selected from the group consisting of:

X1*+X109A+X280S+X391A; X1*+X7K+X109A+X280S+X391A; X1*+X7E+X109A+X280S+X391A; X1*+X7N+X109A+X280S+X391A; X1*+X7Q+X109A+X280S+X391A; X1*+X7L+X109A+X280S+X391A; X1*+X7D+X109A+X280S+X391A; X1*+X109A+X280S+X320A+X391A; X1*+X109A+X280S+X320M+X391A; X1*+X109A+X280S+X320T+X391A; X1*+X109A+X280S+X320V+X391A; X1*+X109A+X280S+X323R+X391A; X1*+X109A+X280S+X320S+X391A; X1*+X109A+X280S+X391V; X1*+X109A+X284R+X391A; X1*+X109A+X284F+X391A; X1*+X109A+X280S+X320A+X323S+X391A; X1*+X109A+X280S+X284F+X391A; X1*+X109A+X280S+X323N+X391A; X1*+X109A+X280S+X323K+X391A; X1*+X109S+X280S+X391A; X1*+X109A+X284H+X391A; X1*+X109A+X280S+X320A+X323N+X391A; X1*+X7A+X109A+X280S+X391A; X1*+X7A+X109A+X280S+X284H+X320A+X323N+X391A; X7A+X284H+X320A+X323N; X7A+X320A+X323N; X320A; X7A+X320A; X1*+X7A+X109A+X280S+X391A; X1*+X109A+X280S+X284H+X391A; X1*+X109A+X280S+X323S+X391A; X1*+X7A+X109A+X280S+X320A+X391A; X1*+X7A+X109A+X280S+X323S+X391A; X1*+X7A+X109A+X280S+X323N+X391A; X1*+X7A+X109A+X280S+X284F+X391A; X1*+X7A+X109A+X280S+X284R+X391A; X1*+X7A+X109A+X280S+X320A+X323S+X391A; X1*+X7A+X109A+X284R+X391A; and X1*+X7A+X109A+X280S+X320A+X323N+X391A, wherein numbering is according to SEQ ID NO: 1 and the variant has at least 80% sequence identity to the amylases set forth in SEQ ID NO: 3.

In one embodiment, the variant comprises modifications in the positions corresponding to the positions of the amino acid sequence set forth in SEQ ID NO: 4, selected from the group consisting of:

X1*+X109A+X280S+X391A; X1*+X7K+X109A+X280S+X391A; X1*+X7E+X109A+X280S+X391A; X1*+X7N+X109A+X280S+X391A; X1*+X7Q+X109A+X280S+X391A; X1*+X7L+X109A+X280S+X391A; X1*+X7D+X109A+X280S+X391A; X1*+X109A+X280S+X320A+X391A; X1*+X109A+X280S+X320M+X391A; X1*+X109A+X280S+X320T+X391A; X1*+X109A+X280S+X320V+X391A; X1*+X109A+X280S+X323R+X391A; X1*+X109A+X280S+X320S+X391A; X1*+X109A+X280S+X391V; X1*+X109A+X284R+X391A; X1*+X109A+X284F+X391A; X1*+X109A+X280S+X320A+X323S+X391A; X1*+X109A+X280S+X284F+X391A; X1*+X109A+X280S+X323N+X391A; X1*+X109A+X280S+X323K+X391A; X1*+X109S+X280S+X391A; X1*+X109A+X284H+X391A; X1*+X109A+X280S+X320A+X323N+X391A; X1*+X7A+X109A+X280S+X391A; X1*+X7A+X109A+X280S+X284H+X320A+X323N+X391A; X7A+X284H+X320A+X323N; X7A+X320A+X323N; X320A; X7A+X320A; X1*+X7A+X109A+X280S+X391A; X1*+X109A+X280S+X284H+X391A; X1*+X109A+X280S+X323S+X391A; X1*+X7A+X109A+X280S+X320A+X391A; X1*+X7A+X109A+X280S+X323S+X391A; X1*+X7A+X109A+X280S+X323N+X391A; X1*+X7A+X109A+X280S+X284F+X391A; X1*+X7A+X109A+X280S+X284R+X391A; X1*+X7A+X109A+X280S+X320A+X323S+X391A; X1*+X7A+X109A+X284R+X391A; and X1*+X7A+X109A+X280S+X320A+X323N+X391A, wherein numbering is according to SEQ ID NO: 1 and the variant has at least 80% sequence identity to the amylases set forth in SEQ ID NO: 4.

In one embodiment, the variant comprises modifications in the positions corresponding to the positions of the amino acid sequence set forth in SEQ ID NO: 5, selected from the group consisting of:

X1*+X109A+X280S+X391A; X1*+X7K+X109A+X280S+X391A; X1*+X7E+X109A+X280S+X391A; X1*+X7N+X109A+X280S+X391A; X1*+X7Q+X109A+X280S+X391A; X1*+X7L+X109A+X280S+X391A; X1*+X7D+X109A+X280S+X391A; X1*+X109A+X280S+X320A+X391A; X1*+X109A+X280S+X320M+X391A; X1*+X109A+X280S+X320T+X391A; X1*+X109A+X280S+X320V+X391A; X1*+X109A+X280S+X323R+X391A; X1*+X109A+X280S+X320S+X391A; X1*+X109A+X280S+X391V; X1*+X109A+X284R+X391A; X1*+X109A+X284F+X391A; X1*+X109A+X280S+X320A+X323S+X391A; X1*+X109A+X280S+X284F+X391A; X1*+X109A+X280S+X323N+X391A; X1*+X109A+X280S+X323K+X391A; X1*+X109S+X280S+X391A; X1*+X109A+X284H+X391A; X1*+X109A+X280S+X320A+X323N+X391A; X1*+X7A+X109A+X280S+X391A; X1*+X7A+X109A+X280S+X284H+X320A+X323N+X391A; X7A+X284H+X320A+X323N; X7A+X320A+X323N; X320A; X7A+X320A; X1*+X7A+X109A+X280S+X391A; X1*+X109A+X280S+X284H+X391A; X1*+X109A+X280S+X323S+X391A; X1*+X7A+X109A+X280S+X320A+X391A; X1*+X7A+X109A+X280S+X323S+X391A; X1*+X7A+X109A+X280S+X323N+X391A; X1*+X7A+X109A+X280S+X284F+X391A; X1*+X7A+X109A+X280S+X284R+X391A; X1*+X7A+X109A+X280S+X320A+X323S+X391A; X1*+X7A+X109A+X284R+X391A; and X1*+X7A+X109A+X280S+X320A+X323N+X391A, wherein numbering is according to SEQ ID NO: 1 and the variant has at least 80% sequence identity to the amylases set forth in SEQ ID NO: 5.

In one embodiment, the variant comprises modifications in the positions corresponding to the positions of the amino acid sequence set forth in SEQ ID NO: 6, selected from the group consisting of:

X1*+X109A+X280S+X391A; X1*+X7K+X109A+X280S+X391A; X1*+X7E+X109A+X280S+X391A; X1*+X7N+X109A+X280S+X391A; X1*+X7Q+X109A+X280S+X391A; X1*+X7L+X109A+X280S+X391A; X1*+X7D+X109A+X280S+X391A; X1*+X109A+X280S+X320A+X391A; X1*+X109A+X280S+X320M+X391A; X1*+X109A+X280S+X320T+X391A; X1*+X109A+X280S+X320V+X391A; X1*+X109A+X280S+X323R+X391A; X1*+X109A+X280S+X320S+X391A; X1*+X109A+X280S+X391V; X1*+X109A+X284R+X391A; X1*+X109A+X284F+X391A; X1*+X109A+X280S+X320A+X323S+X391A; X1*+X109A+X280S+X284F+X391A; X1*+X109A+X280S+X323N+X391A; X1*+X109A+X280S+X323K+X391A; X1*+X109S+X280S+X391A; X1*+X109A+X284H+X391A; X1*+X109A+X280S+X320A+X323N+X391A; X1*+X7A+X109A+X280S+X391A; X1*+X7A+X109A+X280S+X284H+X320A+X323N+X391A; X7A+X284H+X320A+X323N; X7A+X320A+X323N; X320A; X7A+X320A; X1*+X7A+X109A+X280S+X391A; X1*+X109A+X280S+X284H+X391A; X1*+X109A+X280S+X323S+X391A; X1*+X7A+X109A+X280S+X320A+X391A; X1*+X7A+X109A+X280S+X323S+X391A; X1*+X7A+X109A+X280S+X323N+X391A; X1*+X7A+X109A+X280S+X284F+X391A; X1*+X7A+X109A+X280S+X284R+X391A; X1*+X7A+X109A+X280S+X320A+X323S+X391A; X1*+X7A+X109A+X284R+X391A; and X1*+X7A+X109A+X280S+X320A+X323N+X391A, wherein numbering is according to SEQ ID NO: 1 and the variant has at least 80% sequence identity to the amylases set forth in SEQ ID NO: 6.

In one embodiment, the variant comprises modifications in the positions corresponding to the positions of the amino acid sequence set forth in SEQ ID NO: 7, selected from the group consisting of:

X1*+X109A+X280S+X391A; X1*+X7K+X109A+X280S+X391A; X1*+X7E+X109A+X280S+X391A; X1*+X7N+X109A+X280S+X391A; X1*+X7Q+X109A+X280S+X391A; X1*+X7L+X109A+X280S+X391A; X1*+X7D+X109A+X280S+X391A; X1*+X109A+X280S+X320A+X391A; X1*+X109A+X280S+X320M+X391A; X1*+X109A+X280S+X320T+X391A; X1*+X109A+X280S+X320V+X391A; X1*+X109A+X280S+X323R+X391A; X1*+X109A+X280S+X320S+X391A; X1*+X109A+X280S+X391V; X1*+X109A+X284R+X391A; X1*+X109A+X284F+X391A; X1*+X109A+X280S+X320A+X323S+X391A; X1*+X109A+X280S+X284F+X391A; X1*+X109A+X280S+X323N+X391A; X1*+X109A+X280S+X323K+X391A; X1*+X109S+X280S+X391A; X1*+X109A+X284H+X391A; X1*+X109A+X280S+X320A+X323N+X391A; X1*+X7A+X109A+X280S+X391A; X1*+X7A+X109A+X280S+X284H+X320A+X323N+X391A; X7A+X284H+X320A+X323N; X7A+X320A+X323N; X320A; X7A+X320A; X1*+X7A+X109A+X280S+X391A; X1*+X109A+X280S+X284H+X391A; X1*+X109A+X280S+X323S+X391A; X1*+X7A+X109A+X280S+X320A+X391A; X1*+X7A+X109A+X280S+X323S+X391A; X1*+X7A+X109A+X280S+X323N+X391A; X1*+X7A+X109A+X280S+X284F+X391A; X1*+X7A+X109A+X280S+X284R+X391A; X1*+X7A+X109A+X280S+X320A+X323S+X391A; X1*+X7A+X109A+X284R+X391A; and X1*+X7A+X109A+X280S+X320A+X323N+X391A, wherein numbering is according to SEQ ID NO: 1 and the variant has at least 80% sequence identity to the amylases set forth in SEQ ID NO: 7.

In one embodiment, the variant comprises modifications in the positions corresponding to the positions of the amino acid sequence set forth in SEQ ID NO: 8, selected from the group consisting of:

X1*+X109A+X280S+X391A; X1*+X7K+X109A+X280S+X391A; X1*+X7E+X109A+X280S+X391A; X1*+X7N+X109A+X280S+X391A; X1*+X7Q+X109A+X280S+X391A; X1*+X7L+X109A+X280S+X391A; X1*+X7D+X109A+X280S+X391A; X1*+X109A+X280S+X320A+X391A; X1*+X109A+X280S+X320M+X391A; X1*+X109A+X280S+X320T+X391A; X1*+X109A+X280S+X320V+X391A; X1*+X109A+X280S+X323R+X391A; X1*+X109A+X280S+X320S+X391A; X1*+X109A+X280S+X391V; X1*+X109A+X284R+X391A; X1*+X109A+X284F+X391A; X1*+X109A+X280S+X320A+X323S+X391A; X1*+X109A+X280S+X284F+X391A; X1*+X109A+X280S+X323N+X391A; X1*+X109A+X280S+X323K+X391A; X1*+X109S+X280S+X391A; X1*+X109A+X284H+X391A; X1*+X109A+X280S+X320A+X323N+X391A; X1*+X7A+X109A+X280S+X391A; X1*+X7A+X109A+X280S+X284H+X320A+X323N+X391A; X7A+X284H+X320A+X323N; X7A+X320A+X323N; X320A; X7A+X320A; X1*+X7A+X109A+X280S+X391A; X1*+X109A+X280S+X284H+X391A; X1*+X109A+X280S+X323S+X391A; X1*+X7A+X109A+X280S+X320A+X391A; X1*+X7A+X109A+X280S+X323S+X391A; X1*+X7A+X109A+X280S+X323N+X391A; X1*+X7A+X109A+X280S+X284F+X391A; X1*+X7A+X109A+X280S+X284R+X391A; X1*+X7A+X109A+X280S+X320A+X323S+X391A; X1*+X7A+X109A+X284R+X391A; and X1*+X7A+X109A+X280S+X320A+X323N+X391A, wherein numbering is according to SEQ ID NO: 1 and the variant has at least 80% sequence identity to the amylases set forth in SEQ ID NO: 8.

It is preferred that the variant according to the invention comprises a modification at one, two, three, four or five positions selected from the group of X1*, X1A, X7A, X109A, X280S, and X391A. In a more preferred embodiment, the modifications at one, two, three, four or five positions are selected from X1*, X7A, X109A, X280S, and X391A.

In one aspect, the invention relates to variants comprising modifications in the positions corresponding to X1*+X109A+X280S+X391A, X1*+X109A+X284H+X391A, X1*+X109A+X280S+X320A+X323N+X391A, X1*+X7A+X109A+X280S+X391A, and X1*+X7A+X109A+X280S+X284H+X323N+X391A, wherein numbering is according to SEQ ID NO: 1, and wherein the variant has at least 80% sequence identity to SEQ ID NO:1, 2, 3, 4, 5, 6, 7, or 8.

In one embodiment, the invention relates to variants of SEQ ID NO: 1 comprising modifications in the positions corresponding to H1*+G109A+N280S+E391A; H1*+G109A+W284H+E391A; H1*+G109A+N280S+K320A+M323N+E391A; H1*+G7A+G109A+N280S+E391A; and H1*+G7A+G109A+N280S+W284H+M323N+E391A, wherein numbering is according to SEQ ID NO: 1, and wherein the variant has at least 80% sequence identity to SEQ ID NO:1.

In one embodiment, the invention relates to variants of SEQ ID NO: 2 comprising corresponding to H1*+G109A+N280S+E391A; H1*+G109A+W284H+E391A; H1*+G109A+N280S+K320A+M323N+E391A; H1*+G7A+G109A+N280S+E391A; and H1*+G7A+G109A+N280S+W284H+M323N+E391A, wherein numbering is according to SEQ ID NO: 1, and wherein the variant has at least 80% sequence identity to SEQ ID NO: 2.

In one embodiment, the invention relates to variants of SEQ ID NO: 3 comprising corresponding to H1*+G109A+N280S+E391A; H1*+G109A+W284H+E391A; H1*+G109A+N280S+K320A+M323N+E391A; H1*+G7A+G109A+N280S+E391A; and H1*+G7A+G109A+N280S+W284H+M323N+E391A, wherein numbering is according to SEQ ID NO: 1, and wherein the variant has at least 80% sequence identity to SEQ ID NO: 3.

In one embodiment, the invention relates to variants of SEQ ID NO: 4 comprising corresponding to H1*+G109A+N280S+E391A; H1*+G109A+W284H+E391A; H1*+G109A+N280S+K320A+M323N+E391A; H1*+G7A+G109A+N280S+E391A; and H1*+G7A+G109A+N280S+W284H+M323N+E391A, wherein numbering is according to SEQ ID NO: 1, and wherein the variant has at least 80% sequence identity to SEQ ID NO: 4.

In one embodiment, the invention relates to variants of SEQ ID NO: 5 comprising corresponding to H1*+G109A+N280S+E391A; H1*+G109A+W284H+E391A; H1*+G109A+N280S+K320A+M323N+E391A; H1*+G7A+G109A+N280S+E391A; and H1*+G7A+G109A+N280S+W284H+M323N+E391A, wherein numbering is according to SEQ ID NO: 1, and wherein the variant has at least 80% sequence identity to SEQ ID NO: 5.

In one embodiment, the invention relates to variants of SEQ ID NO: 6 comprising corresponding to H1*+G109A+N280S+E391A; H1*+G109A+W284H+E391A; H1*+G109A+N280S+K320A+M323N+E391A; H1*+G7A+G109A+N280S+E391A; and H1*+G7A+G109A+N280S+W284H+M323N+E391A, wherein numbering is according to SEQ ID NO: 1, and wherein the variant has at least 80% sequence identity to SEQ ID NO: 6.

In one embodiment, the invention relates to variants of SEQ ID NO: 7 comprising corresponding to H1*+G109A+N280S+E391A; H1*+G109A+W284H+E391A; H1*+G109A+N280S+K320A+M323N+E391A; H1*+G7A+G109A+N280S+E391A; and H1*+G7A+G109A+N280S+W284H+M323N+E391A, wherein numbering is according to SEQ ID NO: 1, and wherein the variant has at least 80% sequence identity to SEQ ID NO: 7.

In one embodiment, the invention relates to variants of SEQ ID NO: 8 comprising corresponding to H1*+G109A+N280S+E391A; H1*+G109A+W284H+E391A; H1*+G109A+N280S+K320A+M323N+E391A; H1*+G7A+G109A+N280S+E391A; and H1*+G7A+G109A+N280S+W284H+M323N+E391A, wherein numbering is according to SEQ ID NO: 1, and wherein the variant has at least 80% sequence identity to SEQ ID NO: 8.

In one embodiment, the variant of the invention further comprises a modification in one or more positions selected from the group of 140, 181, 182, 183, 184, 195, 206, 243, 260, 304, and 476. In a particular embodiment, the variant of the invention comprises one or more further modifications selected from the group of W140Y/F, R181*, G182*, D183*, G184*, N195FN, I206Y/F, Y243F, E260A/D/C/Q/L/M/F/P/S/W/V/G/H/I/K/N/R/T/Y, G304R/K/E/Q, and G476E/Q/R/K. In one preferred embodiment, the variant according to the invention further comprises substitutions at two, three or four positions selected from the group consisting of G304R, W140YF, E260GHIKNPRTY and G476EQRK. In a more preferred embodiment, the substitutions at the two, three or four positions are selected from the group consisting of G304R, W140Y, E260G and G476K.

In one embodiment, the variant of the invention comprises the modifications corresponding to H1*+G109A+W140Y+D183*+G184*+N195F+I206Y+Y243F+E260G+N280S+G304R+E391A+G 476K, H1*+G109A+W140Y+D183*+G184*+N195F+I206Y+Y243F+E260G+W284H+G304R+E391A+G476K, H1*+G109A+W140Y+D183*+G184*+N195F+I206Y+Y243F+E260G+N280S+G304R+K320A+M 323N+E391A+G476K, H1*+G7A+G109A+W140Y+D183*+G184*+N195F+I206Y+Y243F+E260G+N280S+G304R+E391A+G476K, and H1*+G7A+G109A+W140Y+D183*+G184*+N195F+I206Y+Y243F+E260G+N280S+W284H+G304R+M323N+E391A+G476K, wherein numbering is according to SEQ ID NO: 1, the variant has at least 80% sequence identity to SEQ ID NO: 1, 2, 3, 4, 5, 6, 7, or 8, and is a variant of SEQ ID NO: 1

Essential amino acids in a parent can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the alpha-amylase or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to the parent.

Polynucleotides

The present invention also relates to isolated polynucleotides that encode any of the variants of the present invention. Accordingly, the present invention relates to isolated polynucleotides encoding a variant comprising a modification at one or more positions corresponding to positions: 109, 1, 7, 280, 284, 320, 323, and 3910f the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, wherein the variant has at least 80%, such as at least 85%, at least 90%, such as at least 95%, such as at least 97%, but less than 100% sequence identity with the amino acid sequence set forth in SEQ ID NOs: 1, 2, 3, 4, 5, 6, 7, or 8, and wherein the variant has alpha-amylase activity.

Nucleic Acid Constructs

The present invention also relates to nucleic acid constructs comprising a polynucleotide encoding a variant of the present invention operably linked to one or more (several) control sequences that direct the expression of the coding sequence in a suitable host cell under conditions compatible with the control sequences. Accordingly, the present invention relates to nucleic acid constructs comprising a polynucleotide encoding a variant comprising a modification at one or more positions corresponding to positions: 109, 1, 7, 280, 284, 320, 323, and 391 0f the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, wherein the polynucleotide is operably linked to one or more control sequences that direct the expression of the coding sequence in a suitable host cell under conditions compatible with the control sequences.

A polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, which is recognized by a host cell for expression of the polynucleotide. The promoter sequence contains transcriptional control sequences that mediate the expression of the variant. The promoter may be any nucleic acid sequence that shows transcriptional activity in the host cell including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989, supra.

Examples of suitable promoters for directing the transcription of the nucleic acid constructs of the present invention in a filamentous fungal host cell are the promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* alpha-glucosidase, *Aspergillus niger* glucoamylase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5'-terminus of the polynucleotide encoding the variant. Any leader sequence that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding region naturally linked in translation reading frame with the segment of the coding region that encodes the variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the variant. However, any signal peptide coding region that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding region that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide regions are present at the N-terminus of a variant, the propeptide region is positioned next to the N-terminus of the variant and the signal peptide region is positioned next to the N-terminus of the propeptide region.

It may also be desirable to add regulatory sequences that allow the regulation of the expression of the variant relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide of the present invention, a promoter, and transcriptional and translational stop signals. Accordingly, the present invention relates to recombinant vectors comprising a polynucleotide encoding a variant comprising a modification at one or more positions corresponding to positions 109, 1, 7, 280, 284, 320, 323, and 391of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, a promoter, and transcriptional and translational stop signals. The various nucleotide and control sequences may be joined together to produce a recombinant expression vector that may include one or more (several) convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably comprises one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus licheniformis* or *Bacillus subtilis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3.

The vector preferably comprises an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may comprise additional nucleotide sequences for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a nucleotide sequence that enables a plasmid or vector to replicate in vivo.

More than one copy of a polynucleotide of the present invention may be inserted into the host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra) to obtain substantially pure variants.

Host Cells

The present invention also relates to recombinant host cells, comprising a polynucleotide of the present invention operably linked to one or more (several) control sequences that direct the production of a variant of the present invention. Accordingly, the present invention relates to recombinant host cells, comprising a polynucleotide encoding a variant comprising a modification at one or more positions corresponding to positions 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, wherein the polynucleotide is operably linked to one or more control sequences that direct the production of a variant comprising a modification at one or more positions corresponding to positions 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any gram-positive or gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*. The bacterial host cell may be any *Bacillus* cell, including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell, including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for the expression of the variant; and (b) recovering the variant. Accordingly, the present invention relates to methods of producing a variant, comprising (a) cultivating a host cell comprising an expression vector or a polynucleotide encoding variant comprising a modification at one or more positions corresponding to positions 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1, under conditions suitable for the expression of the variant; and (b) recovering the variant.

In one aspect, the present invention relates to a method of obtaining an alpha-amylase variant, comprising introducing into a parent alpha-amylase a modification at one or more positions corresponding to positions selected from the group consisting of 109, 7, 1, 391, 280, 284, 320, and 323 of the amino acid sequence set forth in SEQ ID NO: 1, and optionally in one or more positions corresponding to positions selected from the group consisting of 140, 181, 182, 183, 184, 195, 206, 243, 260, 304, and 476 of the amino acid sequence as set forth in SEQ ID NO: 1, wherein each modification is independently a substitution or deletion, and the variant has alpha-amylase activity; and recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods may include use of specific antibodies, formation of an enzyme product, or disappearance of an enzyme substrate. For example, an enzyme assay may be used to determine the activity of the variant.

The variant may be recovered by methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure variants.

In an alternative aspect, the variant is not recovered, but rather a host cell of the present invention expressing a variant is used as a source of the variant.

Compositions

The present invention also relates to compositions comprising a variant of the present invention. Accordingly, the present invention relates to compositions comprising a variant comprising a modification at one or more positions corresponding to positions 109, 1, 7, 280, 284, 320, 323, and 391 of the amino acid sequence set forth in SEQ ID NO: 1, and optionally in one or more positions corresponding to positions 140, 181, 182, 183, 184, 195, 206, 243, 260, 304, and 476 of the amino acid sequence as set forth in SEQ ID NO: 1. Preferably, the compositions are enriched in such a variant. The term "enriched" means that the alpha-amylase activity of the composition has been increased, e.g., with an enrichment factor of 1.1.

The composition may comprise a variant as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Bacillus*, e.g. *Bacillus licheniformis* and *Bacillus subtilis*, or the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, e.g., *Humicola insolens* or *Humicola lanuginosa*; or *Trichoderma*, e.g., *Trichoderma harzianum*,

*Trichoderma koningii, Trichoderma longibrachiatum, Trichoderma reesei,* or *Trichoderma viride* or any other host cell herein described.

The compositions may be prepared in accordance with methods known in the art and may be in the form of a liquid or a dry composition. For instance, the composition may be in the form of a granulate or a microgranulate. The variant may be stabilized in accordance with methods known in the art.

According to the invention, the above alpha-amylase variants may typically be a component in a cleaning composition, such as a detergent composition, e.g., a laundry detergent composition or a dishwashing detergent composition. Especially preferred is a liquid laundry detergent composition.

Such cleaning compositions comprise a cleaning/detergent adjunct, preferably a mixture of components. Typically, the cleaning adjunct will be present in the composition in an amount from 0.001 to 99.9 wt %, more typically from 0.01 to 80 wt % cleaning adjunct.

In another preferred aspect the composition comprises one or more surfactants, which may be non-ionic including semi-polar and/or anionic and/or cationic and/or zwitterionic and/or ampholytic and/or semi-polar nonionic and/or mixtures thereof. The surfactants are typically present at a level of from 0.1% to 60% by weight or from 0.5 to 50 wt % or 1 to 40 wt % of the composition.

Uses

The present invention is also directed to methods for using the alpha-amylase variants. The alpha-amylase variants of the invention are useful in detergent compositions, laundry washing, dishwashing and/or cleaning processes at low temperature.

Method of Use

The present invention also relates to a method for cleaning and/or treating a situs inter alia a surface or fabric. In one aspect, such method comprises the steps of optionally washing and/or rinsing said surface or fabric, contacting said surface or fabric with any consumer product disclosed in this specification then optionally washing and/or rinsing said surface or fabric is disclosed.

As used herein, washing includes but is not limited to, scrubbing, and mechanical agitation. Drying of such surfaces or fabrics may be accomplished by any one of the common means employed either in domestic or industrial settings. Such means include but are not limited to forced air or still air drying at ambient or elevated temperatures at pressures between 5 and 0.01 atmospheres in the presence or absence of electromagnetic radiation, including sunlight, infrared, ultraviolet and microwave irradiation. In one aspect, said drying may be accomplished at temperatures above ambient by employing an iron wherein, for example, said fabric may be in direct contact with said iron for relatively short or even extended periods of time and wherein pressure may be exerted beyond that otherwise normally present due to gravitational force. In another aspect, said drying may be accomplished at temperatures above ambient by employing a dryer. Apparatus for drying fabric is well known and it is frequently referred to as a clothes dryer. In addition to clothes such appliances are used to dry many other items including towels, sheets, pillowcases, diapers and so forth and such equipment has been accepted as a standard convenience in many nations of the world substantially replacing the use of clothes lines for drying of fabric. Most dryers in use today use heated air which is passed over and or through the fabric as it is tumbled within the dryer. The air may be heated, for example, either electronically, via gas flame, or even with microwave radiation. Such air may be heated from about 15° C. to about 400° C., from about 25° C. to about 200° C., from about 35° C. to about 100° C., or even from about 40° C. to about 85° C. and used in the dryer to dry a surface and/or a fabric. As will be appreciated by one skilled in the art, the cleaning compositions of the present invention are ideally suited for use in laundry applications. Accordingly, the present invention includes a method for laundering a fabric. The method comprises the steps of contacting a fabric to be laundered with a said cleaning laundry solution comprising at least one embodiment of Applicants' cleaning composition, cleaning additive or mixture thereof. The fabric may comprise most any fabric capable of being laundered in normal consumer or institutional use conditions. The solution preferably has a pH of from about 8 to about 10.5. The compositions may be employed at concentrations of from about 500 ppm to about 15,000 ppm in solution. The water temperatures typically range from about 5° C. to about 90° C. The water to fabric ratio is typically from about 1:1 to about 30:1.

In the Following is Exemplified Detergent Compositions.

TABLE 1

Examples of a granular laundry detergent compositions designed for hand washing or top-loading washing machines. Each granular laundry detergent composition is numbered 1 to 6 in order to differentiate between the different compositions.

|  | 1 (wt %) | 2 (wt %) | 3 (wt %) | 4 (wt %) | 5 (wt %) | 6 (wt %) |
|---|---|---|---|---|---|---|
| Linear alkylbenzenesulfonate | 20 | 22 | 20 | 15 | 20 | 20 |
| $C_{12-14}$ Dimethylhydroxyethyl ammonium chloride | 0.7 | 0.2 | 1 | 0.6 | 0.0 | 0 |
| AE3S | 0.9 | 1 | 0.9 | 0.0 | 0.5 | 0.9 |
| AE7 | 0.0 | 0.0 | 0.0 | 1 | 0.0 | 3 |
| Sodium tripolyphosphate | 5 | 0.0 | 4 | 9 | 2 | 0.0 |
| Zeolite A | 0.0 | 1 | 0.0 | 1 | 4 | 1 |
| 1.6R Silicate ($SiO_2$:$Na_2O$ at ratio 1.6:1) | 7 | 5 | 2 | 3 | 3 | 5 |
| Sodium carbonate | 25 | 20 | 25 | 17 | 18 | 19 |
| Polyacrylate MW 4500 | 1 | 0.6 | 1 | 1 | 1.5 | 1 |
| Random graft copolymer[1] | 0.1 | 0.2 | 0.0 | 0.0 | 0.0 | 0.0 |
| Carboxymethyl cellulose | 1 | 0.3 | 1 | 1 | 1 | 1 |

TABLE 1-continued

Examples of a granular laundry detergent compositions designed for hand washing or top-loading washing machines. Each granular laundry detergent composition is numbered 1 to 6 in order to differentiate between the different compositions.

|  | 1 (wt %) | 2 (wt %) | 3 (wt %) | 4 (wt %) | 5 (wt %) | 6 (wt %) |
|---|---|---|---|---|---|---|
| Protease (Savinase ®, 32.89 mg active/g) | 0.1 | 0.1 | 0.1 | 0.1 |  | 0.1 |
| Lipase-Lipex ® (18 mg active/g) | 0.03 | 0.07 | 0.3 | 0.1 | 0.07 | 0.4 |
| *Amylase of the present invention (mg active) | 0.63 | 1.0 | 2.0 | 0.44 | 0.88 | 0.3 |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| S-ACMC | 0.1 | 0.0 | 0.0 | 0.0 | 0.06 | 0.0 |
| Direct Violet 9 | 0.0 | 0.0 | 0.0003 | 0.0005 | 0.0003 | 0.0 |
| Acid Blue 29 | 0.0 | 0.0 | 0.0 | 0.0 | 0.0 | 0.0003 |
| Sulfate/Moisture | Balance |||||||

*Amylase of the present invention is shown as mgs of active enzyme per 100 g of detergent.

TABLE 2

Other examples (numbered 7 to 12 below in table 2) of granular laundry detergent compositions designed for front-loading automatic washing machines.

|  | 7 (wt %) | 8 (wt %) | 9 (wt %) | 10 (wt %) | 11 (wt %) | 12 (wt %) |
|---|---|---|---|---|---|---|
| Linear alkylbenzenesulfonate | 8 | 7.1 | 7 | 6.5 | 7.5 | 7.5 |
| AE3S | 0 | 4.8 | 0 | 5.2 | 4 | 4 |
| C12-14 Alkylsulfate | 1 | 0 | 1 | 0 | 0 | 0 |
| AE7 | 2.2 | 0 | 3.2 | 0 | 0 | 0 |
| $C_{10-12}$ Dimethyl hydroxyethylammonium chloride | 0.75 | 0.94 | 0.98 | 0.98 | 0 | 0 |
| Crystalline layered silicate ($\delta$-$Na_2Si_2O_5$) | 4.1 | 0 | 4.8 | 0 | 0 | 0 |
| Zeolite A | 5 | 0 | 5 | 0 | 2 | 2 |
| Citric Acid | 3 | 5 | 3 | 4 | 2.5 | 3 |
| Sodium Carbonate | 15 | 20 | 14 | 20 | 23 | 23 |
| Silicate 2R ($SiO_2$:$Na_2O$ at ratio 2:1) | 0.08 | 0 | 0.11 | 0 | 0 | 0 |
| Soil release agent | 0.75 | 0.72 | 0.71 | 0.72 | 0 | 0 |
| Acrylic Acid/Maleic Acid Copolymer | 1.1 | 3.7 | 1.0 | 3.7 | 2.6 | 3.8 |
| Carboxymethylcellulose | 0.15 | 1.4 | 0.2 | 1.4 | 1 | 0.5 |
| Protease-Purafect ® (84 mg active/g) | 0.2 | 0.2 | 0.3 | 0.15 | 0.12 | 0.13 |
| Lipase-Lipex ® (18.00 mg active/g) | 0.05 | 0.15 | 0.1 | 0 | 0 | 0 |
| Cellulase-Celluclean ™ (15.6 mg active/g) | 0 | 0 | 0 | 0 | 0.1 | 0.1 |
| *Amylase of the present invention (mg active) | 4.0 | 2.0 | 1.0 | 0.7 | 6.0 | 3.0 |
| Amylase[4] | 0.15 | 0.04 | 0.03 | — | 0.01 | 0.16 |
| TAED | 3.6 | 4.0 | 3.6 | 4.0 | 2.2 | 1.4 |
| Percarbonate | 13 | 13.2 | 13 | 13.2 | 16 | 14 |
| Na salt of Ethylenediamine-N,N'-disuccinic acid, (S,S) isomer (EDDS) | 0.2 | 0.2 | 0.2 | 0.2 | 0.2 | 0.2 |
| Hydroxyethane di phosphonate (HEDP) | 0.2 | 0.2 | 0.2 | 0.2 | 0.2 | 0.2 |

TABLE 2-continued

Other examples (numbered 7 to 12 below in table 2) of granular laundry detergent compositions designed for front-loading automatic washing machines.

| | 7 (wt %) | 8 (wt %) | 9 (wt %) | 10 (wt %) | 11 (wt %) | 12 (wt %) |
|---|---|---|---|---|---|---|
| $MgSO_4$ | 0.42 | 0.42 | 0.42 | 0.42 | 0.4 | 0.4 |
| Perfume | 0.5 | 0.6 | 0.5 | 0.6 | 0.6 | 0.6 |
| Suds suppressor agglomerate | 0.05 | 0.1 | 0.05 | 0.1 | 0.06 | 0.05 |
| Soap | 0.45 | 0.45 | 0.45 | 0.45 | 0 | 0 |
| Sulphonated zinc phthalocyanine (active) | 0.0007 | 0.0012 | 0.0007 | 0 | 0 | 0 |
| S-ACMC | 0.01 | 0.01 | 0 | 0.01 | 0 | 0 |
| Direct Violet 9 (active) | 0 | 0 | 0.0001 | 0.0001 | 0 | 0 |
| Sulfate/Water & Miscellaneous | | | Balance | | | |

*Amylase of the present invention is shown as mgs of active enzyme per 100 g of detergent.

TABLE 3

Examples of Heavy Duty Liquid laundry detergent compositions (numbered 13 to 18)

| | 13 (wt %) | 14 (wt %) | 15 (wt %) | 16 (wt %) | 17 (wt %) | 18 (wt %) |
|---|---|---|---|---|---|---|
| $C_{12-15}$ Alkylethoxy(1.8)sulfate | 14.7 | 11.6 | | 16.31 | | 17.29 |
| $C_{11.8}$ Alkylbenzene sulfonate | 4.3 | 11.6 | 8.3 | 7.73 | 11.7 | 7.73 |
| $C_{16-17}$ Branched alkyl sulfate | 1.7 | 1.29 | | 3.09 | | 3.3 |
| $C_{12-14}$ Alkyl-9-ethoxylate | 0.9 | 1.07 | | 1.31 | | 1.31 |
| $C_{12}$ dimethylamine oxide | 0.6 | 0.64 | | 1.03 | | 1.03 |
| Citric acid | 3.5 | 0.65 | 3 | 0.66 | 2.27 | 0.67 |
| $C_{12-18}$ fatty acid | 1.5 | 2.32 | 3.6 | 1.52 | 0.82 | 1.52 |
| Sodium Borate (Borax) | 2.5 | 2.46 | 1.2 | 2.53 | | 2.53 |
| Sodium $C_{12-14}$ alkyl ethoxy 3 sulfate | | | | 2.9 | 3.9 | |
| $C_{14-15}$ alkyl 7-ethoxylate | | | | 4.2 | 1.9 | |
| $C_{12-14}$ Alkyl-7-ethoxylate | | | | 1.7 | 0.5 | |
| Ca chloride dihydrate | | | | | 0.045 | |
| Ca formate | 0.09 | 0.09 | | 0.09 | | 0.09 |
| A compound: bis(($C_2H_5O$)($C_2H_4O$)$n$)($CH_3$)—$N^+$—$C_xH_{2x}$—$N^+$—($CH_3$)—bis(($C_2H_5O$)($C_2H_4O$)$n$); n is 20 to 30; x is 3 to 8, optionally sulphated or sulphonated | | | 1.2 | | 0.66 | |
| Random graft co-polymer[1] | | 1.46 | 0.5 | | 0.83 | |
| Ethoxylated Polyethylenimine[2] | 1.5 | 1.29 | | 1.44 | | 1.44 |
| Diethylene triamine pentaacetic acid | 0.34 | 0.64 | | 0.34 | | 0.34 |
| Diethylene triamine penta (methylene phosphonic acid) | | | 0.3 | | 0.3 | |
| 1-hydroxyethyidene-1,1-diphosphonic acid | | | | | 0.18 | |
| Dihydroxybenzene-3,5-disulfonic acid disodium salt hydrate | | | | | | 0.19 |
| Tinopal AMS-GX | | 0.06 | | | | 0.29 |
| Tinopal CBS-X | 0.2 | 0.17 | | 0.29 | | |
| Tinopal TAS-X B36 | | | | | 0.091 | |
| Amphiphilic alkoxylated grease cleaning polymer[3] | 1.28 | 1 | 0.4 | 1.93 | | 1.93 |
| CHEC | | | 0.2 | | | |
| Ethanol | 2 | 1.58 | 1.6 | 5.4 | 1.2 | 3.57 |
| Propylene Glycol | 3.9 | 3.59 | 1.3 | 4.3 | | 3.8 |
| Diethylene glycol | 1.05 | 1.54 | | 1.15 | | 1.15 |
| Polyethylene glycol | 0.06 | 0.04 | | 0.1 | | 0.1 |
| *Amylase of the present invention (mg active) | 15.0 | 10.0 | 5.0 | 8.0 | 4.25 | 11.7 |
| Amylase[4] | | 0.01 | 0.1 | 0.15 | 0.12 | — | 0.05 |
| Monoethanolamine | 3.05 | 2.41 | 0.4 | 1.26 | 0.31 | 1.13 |
| NaOH | 2.44 | 1.8 | | 3.01 | 3.84 | 0.24 |
| Sodium Cumene Sulphonate | | | 1 | | 0.95 | |

TABLE 3-continued

Examples of Heavy Duty Liquid laundry detergent compositions (numbered 13 to 18)

| | 13 (wt %) | 14 (wt %) | 15 (wt %) | 16 (wt %) | 17 (wt %) | 18 (wt %) |
|---|---|---|---|---|---|---|
| Sodium Formate | | 0.11 | | 0.09 | 0.2 | 0.12 |
| Water, Aesthetics (Dyes, perfumes) and Minors (Enzymes including lipase, protease, additional amylase each at 0.2% active protein, solvents, structurants) | | | balance | | | |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethylenimine (MW = 600) with 20 ethoxylate groups per —NH.
[3] Amphiphilic alkoxylated grease cleaning polymer is a polyethylenimine (MW = 600) with 24 ethoxylate groups per —NH and 16 propoxylate groups per —NH
*Amylase of the present invention is shown as mgs of active enzyme per 100 g of detergent.

TABLE 4

Examples of Heavy Duty Liquid laundry detergent composition (numbered 19 to 21)

| | 19 (wt %) | 20 (wt %) | 21 (wt %) |
|---|---|---|---|
| Sodium Alkylbenzene sulfonate | 21.0 | 10.2 | 3.53 |
| $C_{124-18}$ Alkyl 1.5-9-ethoxylate | 18.0 | 6.32 | 0.88 |
| Branched Alkyl Sulfate | | | 2.44 |
| Sodium Alkyl ethoxy 1-3 sulfate | | 1.17 | 14.81 |
| Citric Acid | | 3.14 | 2.05 |
| $C_{12}$ Dimethylamine oxide | | | 0.56 |
| $C_{12-18}$ Fatty acid | 15.0 | 2.59 | 1.48 |
| Protease (Purafect Prime ®, 40.6 mg active/g) | 1.5 | 0.52 | 1.64 |
| Mannanase (Mannaway ®, 11 mg active/g) | 0.1 | 0.06 | |
| Xyloglucanase (Whitezyme ®, 20 mg active/g) | 0.2 | 0.06 | |
| Lipase (ILipex) | 0.1 | 0.2 | 0.05 |
| *Amylase of the present invention (mg active) | 5.9 | 2.3 | 12.8 |
| bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n = from 20 to 30, and x = from 3 to 8, optionally sulphated or sulphonated | 2.0 | 0.63 | |
| Random graft co-polymer[1] | | 1.07 | |
| Ethoxylated Polyethylenimine [2] | 0.8 | | 1.51 |
| Amphiphilic alkoxylated polymer[3] | | | |
| Amylase[4] | | | |
| Phosphonated chelant | 0.8 | 0.41 | 0.53 |
| Hydrotrope | | 0.93 | |
| Brightener | 0.2 | 0.09 | 0.19 |
| Ethoxylated thiophene Hueing Dye | 0.004 | | |
| Minors: dyes, perfume, perfume micro capsules, enzymes, enzyme stabilizers, solvents, structurants, pH modifying agents | Balance | Balance | Balance |

*Amylase of the present invention is shown as mgs of active enzyme per 100 g of detergent.
**Based on total cleaning and/or treatment composition weight, a total of no more than 7% water.

Raw Materials and Notes for Composition Examples 1-21

Linear alkylbenzenesulfonate having an average aliphatic carbon chain length $C_{11}$-$C_{18}$
$C_{12-18}$ Dimethylhydroxyethyl ammonium chloride
AE3S is $C_{12-15}$ alkyl ethoxy (3) sulfate
AE7 is $C_{12-15}$ alcohol ethoxylate, with an average degree of ethoxylation of 7
AE9 is $C_{12-16}$ alcohol ethoxylate, with an average degree of ethoxylation of 9
HSAS is a mid-branched primary alkyl sulfate with carbon chain length of about 16-17 as disclosed in U.S. Pat. Nos. 6,020,303 and 6,060,443
Polyacrylate MW 4500 is supplied by BASF
Carboxymethyl cellulose is Finnfix® V supplied by CP Kelco, Arnhem, Netherlands
CHEC is a cationically modified hydroxyethyl cellulose polymer.
Phosphonate chelants are, for example, diethylenetetraamine pentaacetic acid (DTPA)
Hydroxyethane di phosphonate (HEDP)
Savinase®, Natalase®, Stainzyme®, Lipex®, Celluclean™, Mannaway® and Whitezyme® are all products of Novozymes, Bagsvaerd, Denmark.
Purafect®, Purafect Prime® are products of Genencor International, Palo Alto, California, USA
Fluorescent Brightener 1 is Tinopal® AMS, Fluorescent Brightener 2 is Tinopal® CBS-X, Direct Violet 9 is Pergasol® Violet BN-Z NOBS is sodium nonanoyloxybenzenesulfonate TAED is tetraacetylethylenediamine S-ACMC is carboxymethylcellulose conjugated with C.I. Reactive Blue 19 product name AZO-CM-CELLULOSE Soil release agent is Repel-o-tex® PF Acrylic Acid/Maleic Acid Copolymer is molecular weight 70,000 and acrylate:maleate ratio 70:30 EDDS is a sodium salt of ethylenediamine-N,N'-disuccinic acid, (S,S) isomer Suds suppressor agglomerate is supplied by Dow Corning, Midland, Michigan, USA HSAS is mid-branched alkyl sulfate Liquitint® Violet CT is supplied by Milliken, Spartanburg, South Carolina, USA

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

[2] Polyethyleneimine (MW=600) with 20 ethoxylate groups per —NH.

[3] Amphiphilic alkoxylated polymer is a polyethylenimine (MW 600), prepared from a polymer that is derivatised to contain 24 ethoxylate groups per —NH and 16 Propoxylate groups per —NH. Amylase[4] is any of a) to k) herein (mg active protein).

TABLE 5

Examples of Unit Dose Laundry detergent compositions (numbered 22 to 26). Such unit dose formulations can comprise one or multiple compartments.

| | 22 (wt %) | 23 (wt %) | 24 (wt %) | 25 (wt %) | 26 (wt %) |
|---|---|---|---|---|---|
| Alkylbenzene sulfonic acid | 14.5 | 14.5 | 14.5 | 14.5 | 14.5 |
| $C_{12-18}$ alkyl ethoxy 3 sulfate | 7.5 | 7.5 | 7.5 | 7.5 | 7.5 |
| $C_{12-18}$ alkyl 7-ethoxylate | 13.0 | 13.0 | 13.0 | 13.0 | 13.0 |
| Citric Acid | 0.6 | 0.6 | 0.6 | 0.6 | 0.6 |
| Fatty Acid | 14.8 | 14.8 | 14.8 | 14.8 | 14.8 |
| *Amylase of this invention (mg active) | 6 | 12 | 8 | 2 | 10 |
| Ethoxylated Polyethylenimine[1] | 4.0 | 4.0 | 4.0 | 4.0 | 4.0 |
| Protease (Purafect Prime ®, 40.6 mg active/g) | 1.4 | 2.0 | 0.9 | 1.2 | 0 |
| Cellulase (Celluclean, active protein) | 0.1 | 0.2 | | | 0.1 |
| Amylase[4] (active protein) a) to k) herein | 0.1 | 0.05 | 0.1 | 0.2 | 0.1 |
| Hydroxyethane diphosphonic acid | 1.2 | 1.2 | 1.2 | 1.2 | 1.2 |
| Brightener | 0.3 | 0.3 | 0.3 | 0.3 | 0.3 |
| P-diol | 15.8 | 13.8 | 13.8 | 13.8 | 13.8 |
| Glycerol | 6.1 | 6.1 | 6.1 | 6.1 | 6.1 |
| MEA | 8.0 | 8.0 | 8.0 | 8.0 | 8.0 |
| TIPA | — | — | 2.0 | — | — |
| TEA | — | 2.0 | — | — | — |
| Cumene sulphonate | — | — | — | — | 2.0 |
| cyclohexyl dimethanol | — | — | — | 2.0 | — |
| Water | 10 | 10 | 10 | 10 | 10 |
| Structurant | 0.14 | 0.14 | 0.14 | 0.14 | 0.14 |
| Perfume | 1.9 | 1.9 | 1.9 | 1.9 | 1.9 |
| Buffers (monoethanolamine) | To pH 8.0 | | | | |
| Solvents (1,2 propanediol, ethanol) | To 100% | | | | |

*Amylase of the present invention is shown as mgs of active enzyme per 100 g of detergent.
[1]Polyethylenimine (MW = 600) with 20 ethoxylate groups per —NH.

TABLE 6

Example of Multiple Compartment Unit Dose Composition (numbered 27). Multiple compartment unit dose laundry detergent formulations of the present invention are provided below. In these examples the unit dose has three compartments, but similar compositions can be made with two, four or five compartments. The film used to encapsulate the compartments is polyvinyl alcohol.

| Base composition 1 | 27 (wt %) |
|---|---|
| Glycerol (min 99) | 5.3 |
| 1,2-propanediol | 10.0 |
| Citric Acid | 0.5 |
| Monoethanolamine | 10.0 |
| Caustic soda | — |
| Dequest 2010 | 1.1 |
| Potassium sulfite | 0.2 |
| *Amylase of this invention (mg active) | 8.0 |
| Nonionic Marlipal C24EO7 | 20.1 |
| HLAS | 24.6 |
| Optical brightener FWA49 | 0.2 |
| C12-15 Fatty acid | 16.4 |
| Polymer Lutensit Z96 | 2.9 |
| Polyethyleneimine ethoxylate PEI600 E20 | 1.1 |
| MgCl2 | 0.2 |
| Solvents (1,2 propanediol, ethanol) | To 100% |

TABLE 7

Multi-compartment formulations (numbered as composition 1 or 2 and with a compartment designation [A, B, or C]).

| | Composition | | | | | |
|---|---|---|---|---|---|---|
| | 1 | | | 2 | | |
| Compartment | A | B | C | A | B | C |
| Volume of each compartment | 40 ml | 5 ml | 5 ml | 40 ml | 5 ml | 5 ml |
| Active material in Wt. % | | | | | | |
| Perfume | 1.6 | 1.6 | 1.6 | 1.6 | 1.6 | 1.6 |
| Dyes | <0.01 | <0.01 | <0.01 | <0.01 | <0.01 | <0.01 |
| TiO2 | 0.1 | — | — | — | 0.1 | — |
| Sodium Sulfite | 0.4 | 0.4 | 0.4 | 0.3 | 0.3 | 0.3 |
| Acusol 305 | 1.2 | | | 2 | | |
| Hydrogenated castor oil | 0.14 | 0.14 | 0.14 | 0.14 | 0.14 | 0.14 |
| Base Composition 1 | Add to 100% | Add to 100% | Add to 100% | Add to 100% | Add to 100% | Add to 100% |

*Amylase of the present invention is shown as mgs of active enzyme per 100 g of detergent.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

EXAMPLES pNP-G7 Assay for Determination of Alpha-Amylase Activity

The alpha-amylase activity may be determined by a method employing the G7-pNP substrate. G7-pNP which is an abbreviation for 4,6-ethylidene($G_7$)-p-nitrophenyl($G_1$)-α, D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm). Kits containing G7-pNP substrate and alpha-Glucosidase is manufactured by Roche/Hitachi (cat. No. 11876473).
Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0). The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether ($C_{14}H_{22}O(C_2H_4O)$, (n=9-10))), 1 mM $CaCl_2$, pH8.0.
Procedure:

The amylase sample to be analyzed was diluted in dilution buffer to ensure the pH in the diluted sample is 7. The assay was performed by transferring 20 μl diluted enzyme samples to 96 well microtiter plate and adding 80 μl substrate working solution. The solution was mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Automatic Mechanical Stress Assay (AMSA) for Laundry

In order to assess the wash performance in laundry washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO02/42740 especially the paragraph "Special method embodiments" at page 23-24.

General Wash Performance Description

A test solution comprising water (10° dH), detergent, e.g. 5.1 g/L European liquid detergent as described below and the enzyme of the invention, e.g. at concentration of 0, 0.8 and/or 1.2 mg enzyme protein/L, is prepared. Fabrics stained with starch (e.g. CS-28 from Center For Testmaterials BV, P.O. Box 120, 3133 KT, Vlaardingen, The Netherlands) is added and washed for 20 minutes at 20° C. After thorough rinse under running tap water and drying in the dark, the light intensity or reflectance values of the stained fabrics are subsequently measured as a measure for wash performance. The test with 0 mg enzyme protein/L is used as a blank to obtain a delta remission value. Preferably mechanical action is applied during the wash step, e.g. in the form of shaking, rotating or stirring the wash solution with the fabrics.

The AMSA wash performance experiments were conducted under the experimental conditions specified below:

TABLE 8

| AMSA experimental conditions | |
|---|---|
| Laundry liquid detergent dosage | 5.7 g/L European (EU) liquid detergent (cf. Example 1A), or 0.8 g/L Northern America (US) liquid |

TABLE 8-continued

AMSA experimental conditions

| | |
|---|---|
| Test solution volume | detergent (cf. Example 1B)<br>160 micro L |
| pH | as is |
| Wash time | 5-20 minutes, preferably 20 minutes |
| Temperature | 15-40° C., preferably 20° C. |
| Water hardness | 10° dH, $Ca^{2+}:Mg^{2+}:HCO_3^- = 3:1:6$ |
| Enzyme concentration in test solution | 0.8 and 1.2 Mg/L |
| Test material | CS-28 (Rice starch on cotton) |

Amylase dilution buffer: Amylase was diluted in ultrapure water (MilliQ water) with a small concentration of calcium (0.1 mM) to stabilize the amylase during storage and 0.01% Triton X-100 to reduce risk of adsorption of enzyme protein to containers and pipettes.

Water hardness was adjusted to 10° dH by addition of $CaCl_2$), $MgCl_2$, and $NaHCO_3$ ($Ca^{2+}:Mg^{2+}:HCO_3^-=3:1:4.5$) to the test system. After washing the textiles were flushed in tap water and dried.

The wash performance is measured as the brightness of the color of the textile washed. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance.

Color measurements are made with a professional flatbed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}$$

Results of the AMSA laundry test of different variants are shown in Table 1 and 2. In the result the index is 100. The performance result of the parent alpha-amylase is assigned the value of 100 and the results of the variants are compared to this value.

TOM Wash Performance

Water hardness was adjusted to the strength described below by addition of $CaCl_2$), $MgCl_2$ and $NAHCO_3$. Wash solutions were prepared with desired amount of detergent, temperature and water hardness in a bucket as described below. Detergent was dissolved during magnet stirring for 10 minutes (wash solution was used within 30 to 60 min after preparation).

Temperature and rotation (rpm) in the water bath in the Terg-O-toMeter were set according to the settings below in Table 2. When temperature was adjusted according to settings (tolerance is +/−0.5° C.) wash solution was added to TOM beaker according to the amount described below.

Agitation in the beaker was at 200 rpm. 2 handmade rice starch swatches (HM CS-28), 2 handmade tapioca starch swatches (HM CS-29) and ballast were added to each of the beakers and wash carried out according to time stated below. Swatches were rinsed in cold tap water for 5 minutes and placed in a washing bag and rinsed in washing machine (AEG ÖKO LAVAMAT 86820) on "STIVN" program. The swatches were sorted and left to dry between filter paper in a drying cupboard without heat overnight.

Textile sample HM CS-28 (rice starch on cotton, 5×5 cm, starch applied in 2.5 cm in diameter circle) and HM CS-29 (tapioca starch on cotton, 5×5 cm, starch applied in 2.5 cm in diameter circle) were obtained from Center for Testmaterials BV, P.O. Box 120, 3133 KT Vlaardingen, the Netherlands.

White knitted cotton was used as ballast and was obtained from Warwick Equest Ltd, Unit 55, Consett Business Park, Consett, County Durham, DH8 6BN UK.

TABLE 9

Experimental conditions

| | European conditions using WE SUD | European conditions using WE HDL |
|---|---|---|
| Detergent dosage | 1.87 g/L | 5.30 g/L |
| Enzyme concentration in wash solution | 0.065 mg enzyme protein/L | 0.2 mg enzyme protein/L |
| Water hardness | 20.6° dH<br>(Ca2+:Mg2+:HCO3— = 4:1:7.5) | |
| Test solution volume | 1000 ml | |
| Wash time | 5-15 minutes, preferably 15 minutes | |
| Rotation | 200 rpm | |
| pH | as is | |
| Temperature | 15-40° C., preferably at 15° C. | |

Detergents and test materials were as follows:

| | |
|---|---|
| Laundry liquid detergent | European (WE) conditions: WE SUD as described in Example 2A below and WE HDL as described in Example 2B below (Detergent K). |
| Test material | HM CS-28 (Rice starch on cotton, 5 × 5 cm swatch with starch applied in 2.5 cm in diameter circle), HM CS-29 (tapioca starch on cotton, 5 × 5 cm swatch with starch applied in 2.5 cm in diameter circle). |
| Ballast | White knitted cotton in size 5 × 5 cm added to a total weight of 40 g (40 g including all swatches i.e. ballast and test material). |

The wash performance was measured as the brightness of the color of the textile washed expressed in remission values (REM). Remission measurements were made using a Macbeth 7000 Color Eye spectrophotometer. Each of the dry swatches was measured. As there is a risk of interference from the back-ground, the swatches were placed on top of 2 layers of fabric during the measurement of the remission. The remission was measured at 460 nm. The UV filter was not included. An average result for remission for the swatches was calculated.

The wash performance of different variants is shown in Table 5 as Improvement Factor (IF) and is calculated as shown below:

$$IF = \frac{REM_{Variant} - REM_{Blank}}{REM_{Reference\ enzyme} - REM_{Blank}}$$

Example 1

Wash Performance of Alpha-Amylases Using Automatic Mechanical Stress Assay

In order to assess the wash performance of the alpha-amylases in a detergent base composition, washing experiments may be performed using Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress in a regular, periodic oscillating manner. For further description see WO 02/42740, especially the paragraph "Special method embodiments" at page 23-24.

General Wash Performance Description

A test solution comprising water (6° dH or 15° dH), 0.79 g/L detergent, e.g., model detergent J as described below, and the enzyme of the invention at concentration of 0 or 0.2 mg enzyme protein/L, is prepared. Fabrics stained with starch (CS-28 from Center For Test materials BV, P.O. Box 120, 3133 KT, Vlaardingen, The Netherlands) is added and washed for 10 minutes at 20° C. and 40° C., or alternatively 10 minutes at 20° C. and 30° C. as specified in the examples. After thorough rinse under running tap water and drying in the dark, the light intensity values of the stained fabrics are subsequently measured as a measure for wash performance. The test with 0 mg enzyme protein/L is used as a blank and corresponds to the contribution from the detergent. Preferably mechanical action is applied during the wash step, e.g. in the form of shaking, rotating or stirring the wash solution with the fabrics. The AMSA wash performance experiments may be conducted under the experimental conditions specified below:

TABLE A

Experimental condition

| Detergent | Liquid Model detergent J (see Table B) |
|---|---|
| Detergent dosage | 0.79 g/L |
| Test solution volume | 160 micro L |
| pH | As is |
| Wash time | 10 minutes |
| Temperature | 20° C. or 30° C. |
| Water hardness | 6° dH |
| Enzyme concentration in test | 0.2 mg enzyme protein/L and 0.05 mg enzyme protein/L |
| Test material | CS-28 (Rice starch cotton) |

TABLE B

Model detergent J

| Compound | Content of compound (% w/w) | % active component (% w/w) |
|---|---|---|
| LAS | 5.15 | 5.00 |
| AS | 5.00 | 4.50 |
| AEOS | 14.18 | 10.00 |
| Coco fatty acid | 1.00 | 1.00 |
| AEO | 5.00 | 5.00 |
| MEA | 0.30 | 0.30 |
| MPG | 3.00 | 3.00 |
| Ethanol | 1.50 | 1.35 |
| DTPA (as Na5 salt) | 0.25 | 0.10 |
| Sodium citrate | 4.00 | 4.00 |
| Sodium formate | 1.00 | 1.00 |
| Sodium hydroxide | 0.66 | 0.66 |
| $H_2O$, ion exchanged | 58.95 | 58.95 |

Water hardness was adjusted to 6° dH by addition of $CaCl_2$, $MgCl_2$, and $NaHCO_3$ ($Ca^{2+}:Mg^{2+}:HCO^{3-}=2:1:4.5$) to the test system. After washing the textiles were flushed in tap water and dried.

TABLE C

Experimental condition

| Detergent | Liquid Model detergent A (see Table D) |
|---|---|
| Detergent dosage | 3.33 g/L |
| Test solution volume | 160 micro L |
| pH | As is |
| Wash time | 10 minutes |
| Temperature | 20° C. or 40° C. |
| Water hardness | 15° dH |
| Enzyme concentration in test | 0.2 mg enzyme protein/L, 0.05 mg enzyme protein/L |
| Test material | CS-28 (Rice starch cotton) |

TABLE D

Model detergent A

| Compound | Content of compound (% w/w) | % active component (% w/w) |
|---|---|---|
| LAS | 12.00 | 11.60 |
| AEOS, SLES | 17.63 | 4.90 |
| Soy fatty acid | 2.75 | 2.48 |
| Coco fatty acid | 2.75 | 2.80 |
| AEO | 11.00 | 11.00 |
| Sodium hydroxide | 1.75 | 1.80 |
| Ethanol/Propan-2-ol | 3.00 | 2.70/0.30 |
| MPG | 6.00 | 6.00 |
| Glycerol | 1.71 | 1.70 |
| TEA | 3.33 | 3.30 |
| Sodium formate | 1.00 | 1.00 |
| Sodium citrate | 2.00 | 2.00 |
| DTMPA | 0.48 | 0.20 |
| PCA | 0.46 | 0.18 |
| Phenoxy ethanol | 0.50 | 0.50 |
| $H_2O$, ion exchanged | 33.64 | 33.64 |

Water hardness was adjusted to 15° dH by addition of $CaCl_2$, $MgCl_2$, and $NaHCO_3$ ($Ca^{2+}:Mg^{2+}:HCO^{3-}=4:1:7.5$) to the test system. After washing the textiles were flushed in tap water and dried.

TABLE E

Experimental condition

| Detergent | [Detergent Composition K] |
|---|---|
| Detergent dosage | 5.3 g/L |
| Test solution volume | 160 micro L |
| pH | As is |
| Wash time | 10 minutes |
| Temperature | 20° C. or 40° C. |
| Water hardness | 15° dH |
| Enzyme concentration in test | 0.2 mg enzyme protein/L, 0.05 mg enzyme protein/L |
| Test material | CS-28 (Rice starch cotton) |

TABLE F

Detergent K (as stated in the table 11 below)

| Compound | Content of compound (wt % active) |
|---|---|
| Sodium alkylbenzene sulfonate | 8.7 |
| Sodium alkyl ethoxy 3 sulfate | 1.0 |
| C12-18 alkyl 1.5-7-ethoxylate | 5.3 |
| Citric Acid | 3.1 |
| Optical Brightener | 0.05 |
| Polypropylene Glycol | 1.1 |
| Phosphonated chelant | 0.5 |
| Minors (dyes perfumes, enzymes, | to 100% |

TABLE F-continued

Detergent K (as stated in the table 11 below)

| Compound | Content of compound (wt % active) |
|---|---|
| enzyme stabilisers, solvents, structurants, polymers) and water | |

Water hardness was adjusted to 15° dH by addition of CaCl$_2$, MgCl$_2$, and NaHCO$_3$ (Ca$^{2+}$:Mg$^{2+}$:HCO$^{3-}$=4:1:7.5) to the test system. After washing the textiles were flushed in tap water and dried.

The wash performance is measured as the brightness expressed as the intensity of the light reflected from the sample when illuminated with white light. When the sample is stained the intensity of the reflected light is lower, than that of a clean sample. Therefore, the intensity of the reflected light can be used to measure wash performance.

Color measurements are made with a professional flatbed scanner (EPSON Expression 10000XL, EPSON) used to capture an image of the washed textile.

To extract a value for the light intensity from the scanned images, 48424 Bit Color pixel values from the image are converted into values for red, green and blue (RGB). The intensity value (Int) is calculated by adding the RGB values together as vectors and then taking the length of the resulting vector:

$$Int=\sqrt{r^2+g^2+b^2}$$

The wash performance of the variants according to the invention are shown in the tables below. Table 10 shows the results obtained from the experiment accessing the wash performance in model detergents A (Table D) and J (Table B) in different concentrations (0.05 mg enzyme/L detergent and 0.2 mg enzyme/L detergent), and at different temperatures (20° C. and 40° C.). Table 11 shows the results obtained from the experiment accessing the wash performance in detergent K (Table F) in different concentrations (0.05 mg enzyme/L detergent and 0.2 mg enzyme/L detergent) and at different temperatures (20° C. and 40° C.). The mutations in the variants are indicated in Tables 10 and 11 as amylases having the amino acid sequence as set forth in SEQ ID NO: 2, and additionally consisting of the noted substitution(s) where the amino acid numbering corresponds to the positions of the amino acid sequence set forth in SEQ ID NO: 1.

TABLE 10

Results of wash performance in Model detergents

| Mutations | 0.05 mg/ L-A-20C | 0.2 mg/ L-A-20C | 0.05 mg/ L-A-40C | 0.2 mg/ L-A-40C | 0.05 mg/ L-J-20C | 0.2 mg/ L-J-20C | 0.05 mg/ L-J-30C | 0.2 mg/ L-J-30C |
|---|---|---|---|---|---|---|---|---|
| SEQ ID NO: 2 + H1* + G7A + G109A + N280S + W284H + K320A + M323N + E391A | 4.7 | 1.5 | 2.3 | 1.1 | 2.7 | 1.1 | 3.5 | 1.5 |
| SEQ ID NO: 2 + G7A + W284H + K320A + M323N | 4.7 | 1.4 | 1.8 | 1.0 | 3.0 | 1.1 | 2.0 | 1.2 |
| SEQ ID NO: 2 + G7A + K320A + M323N | 4.3 | 1.6 | 2.0 | 1.0 | 2.0 | 1.1 | 2.0 | 1.2 |
| SEQ ID NO: 2 + K320A | 4.7 | 1.3 | 2.3 | 1.0 | 3.7 | 1.0 | 4.5 | 1.5 |
| SEQ ID NO: 2 + G7A + K320A | 4.3 | 1.4 | 2.3 | 1.1 | 3.3 | 1.1 | 2.5 | 1.3 |
| SEQ ID NO: 2 + H1* + G7A + G109A + N280S + E391A | 1.7 | 1.2 | 1.3 | 1.3 | 1.5 | 1.3 | 1.1 | 1.4 |
| SEQ ID NO: 2 + H1* + G109A + N280S + W284H + E391A | 2.3 | 1.7 | 2.8 | 1.4 | 5.0 | 2.0 | 5.5 | 1.8 |
| SEQ ID NO: 2 + H1* + G109A + N280S + E391A | 0.8 | 1.0 | 1.0 | 1.1 | 1.0 | 1.1 | 1.3 | 1.1 |
| SEQ ID NO: 2 + H1* + G109A + N280S + M323S + E391A | 1.3 | 1.9 | 1.5 | 1.3 | 1.5 | 1.5 | 1.6 | 1.6 |
| SEQ ID NO: 2 + H1* + G7A + G109A + N280S + K320A + E391A | 1.5 | 1.2 | 1.3 | 1.2 | 1.2 | 1.1 | 1.7 | 1.1 |
| SEQ ID NO: 2 + H1* + G7A + G109A + N280S + M323S + E391A | 1.3 | 1.3 | 1.5 | 1.1 | 1.0 | 1.0 | 1.2 | 1.1 |
| SEQ ID NO: 2 + H1* + G7A + G109A + N280S + M323N + E391A | 1.4 | 1.3 | 1.3 | 1.2 | 1.0 | 1.2 | 1.6 | 1.1 |
| SEQ ID NO: 2 + H1* + G7A + G109A + N280S + W284F + E391A | 1.3 | 1.4 | 1.3 | 1.2 | 0.9 | 1.2 | 1.6 | 1.0 |
| SEQ ID NO: 2 + H1* + G7A + G109A + N280S + W284R + E391A | 1.1 | 1.3 | 1.0 | 1.0 | 0.7 | 1.2 | 1.4 | 0.9 |
| SEQ ID NO: 2 + H1* + G7A + G109A + N280S + K320A + M323S + E391A | 1.1 | 1.3 | 0.9 | 1.1 | 0.5 | 1.2 | 0.8 | 1.0 |
| SEQ ID NO: 2 + H1* + G7A + G109A + W284R + E391A | 1.0 | 1.2 | 0.9 | 1.1 | 0.6 | 1.1 | 1.1 | 1.0 |
| SEQ ID NO: 2 + H1* + G7A + G109A + N280S + K320A + M323N + E391A | 1.0 | 1.2 | 0.8 | 1.0 | 0.8 | 1.2 | 0.9 | 1.0 |

TABLE 11

Results of wash performance in detergent K

| Mutations | 0.05 mg/L- Det. KAriel-20 C. | 0.2 mg/L- Det. K Ariel-20 C. | 0.05 mg/L- Det. KAriel-40 C. | 0.2 mg/L- Det. KAriel-40 C. |
|---|---|---|---|---|
| Reference - SEQ ID NO: 2 | 1.0 | 1.0 | 1.0 | 1.0 |
| SEQ ID NO: 2 + H1* + G109A + N280S + E391A | 1.1 | 1.0 | 2.0 | 1.1 |
| SEQ ID NO: 2 + H1* + G7K + G109A + N280S + E391A | 1.2 | 1.6 | 0.9 | 1.1 |
| SEQ ID NO: 2 + H1* + G7E + G109A + N280S + E391A | 1.2 | 1.6 | 0.6 | 1.0 |

TABLE 11-continued

Results of wash performance in detergent K

| Mutations | 0.05 mg/L- Det. KAriel-20 C. | 0.2 mg/L- Det. K Ariel-20 C. | 0.05 mg/L- Det. KAriel-40 C. | 0.2 mg/L- Det. KAriel-40 C. |
|---|---|---|---|---|
| SEQ ID NO: 2 + H1* + G7N + G109A + N280S + E391A | 0.9 | 1.6 | 1.0 | 1.1 |
| SEQ ID NO: 2 + H1* + G7Q + G109A + N280S + E391A | 1.6 | 1.6 | 1.1 | 1.1 |
| SEQ ID NO: 2 + H1* + G7L + G109A + N280S + E391A | 1.6 | 1.6 | 1.4 | 1.3 |
| SEQ ID NO: 2 + H1* + G7D + G109A + N280S + E391A | 1.9 | 1.6 | 1.5 | 1.3 |
| SEQ ID NO: 2 + H1* + G109A + N280S + K320A + E391A | 0.4 | 0.9 | 1.0 | 1.3 |
| SEQ ID NO: 2 + H1* + G109A + N280S + K320M + E391A | 1.5 | 1.1 | 1.8 | 1.3 |
| SEQ ID NO: 2 + H1* + G109A + N280S + K320T + E391A | 1.3 | 1.1 | 1.5 | 1.1 |
| SEQ ID NO: 2 + H1* + G109A + N280S + K320V + E391A | 1.0 | 0.9 | 1.7 | 1.1 |
| SEQ ID NO: 2 + H1* + G109A + N280S + M323R + E391A | 0.7 | 0.9 | 1.3 | 1.0 |
| SEQ ID NO: 2 + H1* + G109A + N280S + K320S + E391A | 1.8 | 1.3 | 1.8 | 1.3 |
| SEQ ID NO: 2 + H1* + G109A + N280S + E391V | 1.3 | 1.1 | 2.0 | 1.3 |
| SEQ ID NO: 2 + H1* + G109A + W284R + E391A | 1.2 | 1.3 | 1.2 | 1.2 |
| SEQ ID NO: 2 + H1* + G109A + W284F + E391A | 1.7 | 1.3 | 1.8 | 1.2 |
| SEQ ID NO: 2 + H1* + G109A + N280S + K320A + M323S + E391A | 2.0 | 1.4 | 1.4 | 1.2 |
| SEQ ID NO: 2 + H1* + G109A + N280S + W284F + E391A | 0.9 | 0.9 | 1.3 | 1.0 |
| SEQ ID NO: 2 + H1* + G109A + N280S + M323N + E391A | 2.0 | 1.6 | 2.0 | 1.3 |
| SEQ ID NO: 2 + H1* + G109A + N280S + M323K + E391A | 2.3 | 1.6 | 2.0 | 1.6 |
| SEQ ID NO: 2 + H1* + G109S + N280S + E391A | 2.5 | 1.3 | 2.3 | 1.1 |
| SEQ ID NO: 2 + H1* + G109A + W284H + E391A | 1.5 | 1.2 | 1.3 | 1.1 |
| SEQ ID NO: 2 + H1* + G109A + N280S + K320A + M323N + E391A | 1.6 | 1.1 | 1.2 | 1.1 |
| SEQ ID NO: 2 + H1* + G7A + G109A + N280S + E391A | 1.5 | 1.4 | 1.2 | 1.2 |

As can be seen from Table 10 and Table 11, all the tested variants have an improved wash performance compared to the reference (SEQ ID NO: 2) in at least one of the tested conditions.

Example 2—Wash Performance in TOM of Alpha-Amylases in Liquid Detergent K

The wash performance of the tested variant and corresponding parent alpha-amylase (SEQ ID NO: 2) were tested as described above for TOM scale wash. The mutations in the variants are indicated as amylases having the amino acid sequence as set forth in SEQ ID NO: 2, and additionally consisting of the noted substitution(s) where the amino acid numbering corresponds to the positions of the amino acid sequence set forth in SEQ ID NO: 1. The detergent used was detergent K. The results are given as (performance of variant minus performance of blank) divided by (performance of parent minus performance of blank).

TABLE 12

Wash performance in TOM scale

| | Detergent K [WE HDL] | |
|---|---|---|
| | IF HM CS-28 | IF HM CS-29 |
| Reference/SEQ ID NO: 2) | 1.00 | 1.00 |
| SEQ ID NO: 2 + H1* + G109A + W284H + E391A | 1.28 | 1.58 |
| SEQ ID NO: 2 + H1* + G109A + N280S + K320A + M323N + E391A | 1.13 | 1.61 |
| SEQ ID NO: 2 + H1* + G7A + G109A + N280S + E391A | 1.22 | 2.02 |

TABLE 13

Wash performance in TOM scale

| | Det. K | |
|---|---|---|
| 1 L, 5 min wash 0.13 mg enzyme protein/L | IF HM CS-29 | IF HM CS-26 |
| Reference SEQ ID NO: 2 | 1.00 | 1.00 |
| SEQ ID NO: 2 + H1* + G109A + W284H + E391A | 1.00 | 1.00 |
| SEQ ID NO: 2 + H1* + G109A + N280S + K320A + M323N + E391A | 1.08 | 1.11 |
| SEQ ID NO: 2 + H1* + G7A + G109A + N280S + E391A | 1.10 | 1.13 |

TABLE 14

Wash Performance in Full Scale Washing Machine Test

| | Det. K | |
|---|---|---|
| Full scale, 0.072 mg enzyme protein/L | IF HM CS-29 | IF HM CS-26 |
| Reference SEQ ID NO: 2 | 1.00 | 1.00 |
| SEQ ID NO: 2 + H1* + G109A + W284H + E391A | 1.07 | 1.02 |
| SEQ ID NO: 2 + H1* + G109A + N280S + K320A + M323N + E391A | 1.22 | 1.32 |
| SEQ ID NO: 2 + H1* + G7A + G109A + N280S + E391A | 1.32 | 1.41 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A variant of a parent alpha-amylase, wherein said variant comprises:
   (i) substitutions corresponding to H1*, G109A, N280S, E391A, and G7A, wherein the amino acid numbering corresponds to the positions of the amino acid sequence set forth in SEQ ID NO: 1,
   (ii) at least 90% but less than 100% sequence identity with the amino acid sequence set forth in SEQ ID NO: 2
   (iii) has alpha-amylase activity, and
   (iv) has improved wash performance compared to the parent amino acid sequence set forth in SEQ ID NO: 2.

2. The variant of according to claim 1, wherein said variant has at least 95%, but less than 100%, sequence identity to the amino acid sequence of the parent alpha-amylase.

3. The variant according to claim 2, wherein said variant consists of modifications in the positions corresponding to the positions of the amino acid sequence set forth in SEQ ID NO: 1, selected from the group consisting of:
   H1*+G7A+G109A+N280S+W284H+K320A+M323N+E391A;
   H1*+G7A+G109A+N280S+K320A+E391A;
   H1*+G7A+G109A+N280S+M323S+E391A;
   H1*+G7A+G109A+N280S+M323N+E391A;
   H1*+G7A+G109A+N280S+W284F+E391A;
   H1*+G7A+G109A+N280S+W284R+E391A;
   H1*+G7A+G109A+N280S+K320A+M323S+E391A; and
   H1*+G7A+G109A+N280S+K320A+M323N+E391A.

4. The variant according to claim 1, wherein said variant comprises modifications in the positions corresponding to the positions of the amino acid sequence set forth in SEQ ID NO: 1, selected from the group consisting of:
   H1*+G7A+G109A+N280S+W284H+K320A+M323N+E391A;
   H1*+G7A+G109A+N280S+K320A+E391A;
   H1*+G7A+G109A+N280S+M323S+E391A;
   H1*+G7A+G109A+N280S+M323N+E391A;
   H1*+G7A+G109A+N280S+W284F+E391A;
   H1*+G7A+G109A+N280S+W284R+E391A;
   H1*+G7A+G109A+N280S+K320A+M323S+E391A; and
   H1*+G7A+G109A+N280S+K320A+M323N+E391A.

5. The variant according to claim 1, wherein said parent alpha-amylase is selected from the amino acid sequences set forth in SEQ ID NOs: 1 and 2, or any alpha-amylase having at least 90% sequence identity to the amino acid sequence set forth in SEQ ID NO: 2.

6. The variant according to claim 1, wherein said parent alpha-amylase comprises or consists of the amino acid sequence set forth in SEQ ID NO: 2.

7. The variant of according to claim 1, wherein said variant has at least 98%, but less than 100%, sequence identity to the amino acid sequence of the parent alpha-amylase.

8. The variant according to claim 1, wherein said variant has at least 95% sequence identity with the amino acid sequence set forth in SEQ ID NO: 2.

9. A polynucleotide encoding said variant according to claim 1.

10. A nucleic acid construct comprising said polynucleotide according to claim 9.

11. An expression vector comprising said polynucleotide according to claim 9.

12. A host cell comprising said polynucleotide according to claim 9.

13. A method of producing an alpha-amylase variant, comprising:
   a. cultivating said host cell according to claim 12 under conditions suitable for expression of said variant; and
   b. recovering said variant.

14. A method for obtaining an alpha-amylase variant, comprising introducing into a parent alpha-amylase substitutions corresponding to H1*, G109A, N280S, E391A, and G7A, wherein the amino acid numbering corresponds to the positions of the amino acid sequence set forth in SEQ ID NO: 1, wherein said parent alpha-amylase has at least 90% sequence identity with the amino acid sequence set for in SEQ ID NO: 2, and wherein said variant has alpha-amylase activity; and recovering said variant.

15. The method of claim 14, wherein the variant has at least 95% sequence identity with the amino acid sequence set forth in SEQ ID NO: 2.

16. The method of claim 14, wherein the variant has at least 98% sequence identity with the amino acid sequence set forth in SEQ ID NO: 2.

17. The variant according to claim 1, wherein said variant consists of modifications in the positions corresponding to the positions of the amino acid sequence set forth in SEQ ID NO: [2]1, selected from the group consisting of:
H1*+G7A+G109A+N280S+W284H+K320A+M323N+E391A;
H1*+G7A+G109A+N280S+K320A+E391A;
H1*+G7A+G109A+N280S+M323S+E391A;
H1*+G7A+G109A+N280S+M323N+E391A;
H1*+G7A+G109A+N280S+W284F+E391A;
H1*+G7A+G109A+N280S+W284R+E391A;
H1*+G7A+G109A+N280S+K320A+M323S+E391A; and
H1*+G7A+G109A+N280S+K320A+M323N+E391A.

* * * * *

SEQUENCE LISTING

<160> NUMBER OF SEQ ID NOS: 8

<210> SEQ ID NO 1
<211> LENGTH: 485
<212> TYPE: PRT
<213> ORGANISM: Bacillus halmapalus

<400> SEQUENCE: 1

```
His His Asn Gly Thr Asn Gly Thr Met Met Gln Tyr Phe Glu Trp His
  1               5                  10                  15

Leu Pro Asn Asp Gly Asn His Trp Asn Arg Leu Arg Asp Asp Ala Ser
             20                  25                  30

Asn Leu Arg Asn Arg Gly Ile Thr Ala Ile Trp Ile Pro Pro Ala Trp
         35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365
```

```
Gly Asp Tyr Tyr Gly Ile Pro Thr His Ser Val Pro Ala Met Lys Ala
        370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                    405                 410                 415

Gly Asn Thr Thr His Pro Asn Ser Gly Leu Ala Thr Ile Met Ser Asp
                    420                 425                 430

Gly Pro Gly Gly Glu Lys Trp Met Tyr Val Gly Gln Asn Lys Ala Gly
                435                 440                 445

Gln Val Trp His Asp Ile Thr Gly Asn Lys Pro Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 2
<211> LENGTH: 483
<212> TYPE: PRT
<213> ORGANISM: Bacillus halmapalus

<400> SEQUENCE: 2

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Tyr Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Lys Ala Trp Asp Trp Glu Val Asp Ser Glu
            180                 185                 190

Phe Gly Asn Tyr Asp Tyr Leu Met Tyr Ala Asp Tyr Asp Met Asp His
        195                 200                 205

Pro Glu Val Val Asn Glu Leu Arg Arg Trp Gly Glu Trp Tyr Thr Asn
210                 215                 220

Thr Leu Asn Leu Asp Gly Phe Arg Ile Asp Ala Val Lys His Ile Lys
225                 230                 235                 240

Phe Ser Phe Thr Arg Asp Trp Leu Thr His Val Arg Asn Ala Thr Gly
                245                 250                 255
```

Lys Gly Met Phe Ala Val Ala Glu Phe Trp Lys Asn Asp Leu Gly Ala
            260                 265                 270

Leu Glu Asn Tyr Leu Asn Lys Thr Asn Trp Asn His Ser Val Phe Asp
        275                 280                 285

Val Pro Leu His Tyr Asn Leu Tyr Asn Ala Ser Asn Ser Arg Gly Asn
290                 295                 300

Tyr Asp Met Ala Lys Leu Leu Asn Gly Thr Val Val Gln Lys His Pro
305                 310                 315                 320

Met His Ala Val Thr Phe Val Asp Asn His Asp Ser Gln Pro Gly Glu
                325                 330                 335

Ser Leu Glu Ser Phe Val Gln Glu Trp Phe Lys Pro Leu Ala Tyr Ala
            340                 345                 350

Leu Ile Leu Thr Arg Glu Gln Gly Tyr Pro Ser Val Phe Tyr Gly Asp
        355                 360                 365

Tyr Tyr Gly Ile Pro Thr His Ser Val Pro Ala Met Lys Ala Lys Ile
370                 375                 380

Asp Pro Ile Leu Glu Ala Arg Gln Asn Phe Ala Tyr Gly Thr Gln His
385                 390                 395                 400

Asp Tyr Phe Asp His His Asn Ile Ile Gly Trp Thr Arg Glu Gly Asn
                405                 410                 415

Thr Thr His Pro Asn Ser Gly Leu Ala Thr Ile Met Ser Asp Gly Pro
            420                 425                 430

Gly Gly Glu Lys Trp Met Tyr Val Gly Gln Asn Lys Ala Gly Gln Val
        435                 440                 445

Trp His Asp Ile Thr Gly Asn Lys Pro Gly Thr Val Thr Ile Asn Ala
450                 455                 460

Asp Gly Trp Ala Asn Phe Ser Val Asn Lys Gly Ser Val Ser Ile Trp
465                 470                 475                 480

Val Lys Arg

<210> SEQ ID NO 3
<211> LENGTH: 485
<212> TYPE: PRT
<213> ORGANISM: Bacillus sp.

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

```
Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
            165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
            210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
            275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
            325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 4
<211> LENGTH: 485
<212> TYPE: PRT
<213> ORGANISM: Bacillus sp.

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
```

```
            20                  25                  30
Asn Leu Lys Ser Lys Gly Ile Thr Ala Val Trp Ile Pro Pro Ala Trp
         35                  40                  45
Lys Gly Ala Ser Gln Asn Asp Val Gly Tyr Gly Ala Tyr Asp Leu Tyr
 50                  55                  60
Asp Leu Gly Glu Phe Asn Gln Lys Gly Thr Val Arg Thr Lys Tyr Gly
 65                  70                  75                  80
Thr Arg Ser Gln Leu Gln Ala Ala Val Thr Ser Leu Lys Asn Asn Gly
                 85                  90                  95
Ile Gln Val Tyr Gly Asp Val Val Met Asn His Lys Gly Gly Ala Asp
                100                 105                 110
Ala Thr Glu Met Val Arg Ala Val Glu Val Asn Pro Asn Asn Arg Asn
                115                 120                 125
Gln Glu Val Thr Gly Glu Tyr Thr Ile Glu Ala Trp Thr Arg Phe Asp
                130                 135                 140
Phe Pro Gly Arg Gly Asn Thr His Ser Ser Phe Lys Trp Arg Trp Tyr
145                 150                 155                 160
His Phe Asp Gly Val Asp Trp Asp Gln Ser Arg Arg Leu Asn Asn Arg
                165                 170                 175
Ile Tyr Lys Phe Arg Gly His Gly Lys Ala Trp Asp Trp Glu Val Asp
                180                 185                 190
Thr Glu Asn Gly Asn Tyr Asp Tyr Leu Met Tyr Ala Asp Ile Asp Met
                195                 200                 205
Asp His Pro Glu Val Val Asn Glu Leu Arg Asn Trp Gly Val Trp Tyr
                210                 215                 220
Thr Asn Thr Leu Gly Leu Asp Gly Phe Arg Ile Asp Ala Val Lys His
225                 230                 235                 240
Ile Lys Tyr Ser Phe Thr Arg Asp Trp Ile Asn His Val Arg Ser Ala
                245                 250                 255
Thr Gly Lys Asn Met Phe Ala Val Ala Glu Phe Trp Lys Asn Asp Leu
                260                 265                 270
Gly Ala Ile Glu Asn Tyr Leu Gln Lys Thr Asn Trp Asn His Ser Val
                275                 280                 285
Phe Asp Val Pro Leu His Tyr Asn Leu Tyr Asn Ala Ser Lys Ser Gly
                290                 295                 300
Gly Asn Tyr Asp Met Arg Asn Ile Phe Asn Gly Thr Val Val Gln Arg
305                 310                 315                 320
His Pro Ser His Ala Val Thr Phe Val Asp Asn His Asp Ser Gln Pro
                325                 330                 335
Glu Glu Ala Leu Glu Ser Phe Val Glu Trp Phe Lys Pro Leu Ala
                340                 345                 350
Tyr Ala Leu Thr Leu Thr Arg Glu Gln Gly Tyr Pro Ser Val Phe Tyr
                355                 360                 365
Gly Asp Tyr Tyr Gly Ile Pro Thr His Gly Val Pro Ala Met Arg Ser
                370                 375                 380
Lys Ile Asp Pro Ile Leu Glu Ala Arg Gln Lys Tyr Ala Tyr Gly Lys
385                 390                 395                 400
Gln Asn Asp Tyr Leu Asp His His Asn Ile Ile Gly Trp Thr Arg Glu
                405                 410                 415
Gly Asn Thr Ala His Pro Asn Ser Gly Leu Ala Thr Ile Met Ser Asp
                420                 425                 430
Gly Ala Gly Gly Ser Lys Trp Met Phe Val Gly Arg Asn Lys Ala Gly
                435                 440                 445
```

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 5
<211> LENGTH: 485
<212> TYPE: PRT
<213> ORGANISM: Bacillus sp.

<400> SEQUENCE: 5

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro

```
            325                 330                 335
Glu Glu Ala Leu Glu Ser Phe Val Glu Glu Trp Phe Lys Pro Leu Ala
            340                 345                 350

Cys Ala Leu Thr Leu Thr Arg Asp Gln Gly Tyr Pro Ser Val Phe Tyr
            355                 360                 365

Gly Asp Tyr Tyr Gly Ile Pro Thr His Gly Val Pro Ala Met Lys Ser
        370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
            435                 440                 445

Gln Val Trp Arg Asp Ile Thr Gly Asn Arg Ser Gly Thr Val Thr Ile
        450                 455                 460

Asn Ala Asp Gly Trp Gly Asn Phe Ser Val Asn Gly Gly Ser Val Ser
465                 470                 475                 480

Ile Trp Val Asn Asn
            485

<210> SEQ ID NO 6
<211> LENGTH: 483
<212> TYPE: PRT
<213> ORGANISM: Bacillus sp.

<400> SEQUENCE: 6

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Ile Asp Met Asp His
        195                 200                 205
```

```
Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Arg Ser Lys Ile
    370                 375                 380

Asp Pro Ile Leu Glu Ala Arg Gln Lys Tyr Ala Tyr Gly Pro Gln His
385                 390                 395                 400

Asp Tyr Leu Asp His Pro Asp Val Ile Gly Trp Thr Arg Glu Gly Asp
                405                 410                 415

Ser Ser His Pro Lys Ser Gly Leu Ala Thr Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 7
<211> LENGTH: 483
<212> TYPE: PRT
<213> ORGANISM: Bacillus licheniformis

<400> SEQUENCE: 7

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95
```

Val Tyr Gly Asp Val Val Ile Asn His Lys Gly Ala Asp Ala Thr
                100                 105                 110

Glu Asp Val Thr Ala Val Glu Val Asp Pro Ala Asp Arg Asn Arg Val
115                 120                 125

Ile Ser Gly Glu His Leu Ile Lys Ala Trp Thr His Phe His Phe Pro
        130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 8
<211> LENGTH: 481
<212> TYPE: PRT
<213> ORGANISM: Artificial sequence
<220> FEATURE:
<223> OTHER INFORMATION: Synthetic

<400> SEQUENCE: 8

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Thr Ser
        35                  40                  45

Gln Ala Asp Val Gly Tyr Gly Ala Tyr Asp Leu Tyr Asp Leu Gly Glu
    50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Gly Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp His Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Ala Trp Asp Trp Glu Val Ser Asn Glu Asn Gly Asn Tyr Asp
            180                 185                 190

Tyr Leu Met Tyr Ala Asp Ile Asp Tyr Asp His Pro Asp Val Ala Ala
        195                 200                 205

Glu Ile Lys Arg Trp Gly Thr Trp Tyr Ala Asn Glu Leu Gln Leu Asp
    210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Gln Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

-continued

```
Glu Ser Gly Tyr Pro Gln Val Phe Tyr Gly Asp Met Tyr Gly Thr Lys
        355                 360                 365

Gly Asp Ser Gln Arg Glu Ile Pro Ala Leu Lys His Lys Ile Glu Pro
        370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
                405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
        435                 440                 445

Asp Ile Thr Gly Asn Arg Ser Glu Pro Val Val Ile Asn Ser Glu Gly
        450                 455                 460

Trp Gly Glu Phe His Val Asn Gly Gly Ser Val Ser Ile Tyr Val Gln
465                 470                 475                 480

Arg
```